(12) United States Patent
Bouton et al.

(10) Patent No.: US 10,987,509 B2
(45) Date of Patent: Apr. 27, 2021

(54) SYSTEMS INCLUDING NEUROMUSCULAR STIMULATION CUFF

(71) Applicant: Battelle Memorial Institute, Columbus, OH (US)

(72) Inventors: Chad E. Bouton, Powell, OH (US); Jeffrey Friend, Columbus, OH (US)

(73) Assignee: BATTELLE MEMORIAL INSTITUTE, Columbus, OH (US)

( * ) Notice: Subject to any disclaimer, the term of this patent is extended or adjusted under 35 U.S.C. 154(b) by 38 days.

(21) Appl. No.: 16/371,417

(22) Filed: Apr. 1, 2019

(65) Prior Publication Data

US 2019/0224473 A1    Jul. 25, 2019

Related U.S. Application Data

(60) Continuation of application No. 15/872,272, filed on Jan. 16, 2018, now Pat. No. 10,293,151, which is a (Continued)

(51) Int. Cl.
*A61B 5/00* (2006.01)
*A61N 1/04* (2006.01)
(Continued)

(52) U.S. Cl.
CPC ......... *A61N 1/0484* (2013.01); *A61N 1/0452* (2013.01); *A61N 1/0456* (2013.01);
(Continued)

(58) Field of Classification Search
USPC ............................................ 607/48; 600/372
See application file for complete search history.

(56) References Cited

U.S. PATENT DOCUMENTS 6,609,018 B2 *  8/2003  Cory ................. A61B 5/04001
                                                          600/393
2004/0249302 A1   12/2004  Donoghue et al.
(Continued)

FOREIGN PATENT DOCUMENTS

WO    WO 2012/139124 A1    10/2012
WO    WO 2012/143850 A1    10/2012
WO    WO 2012/155917 A2    11/2012

OTHER PUBLICATIONS

"FDA approves BrainsGate stroke treatment study", Jul. 26, 2012, Globes' correspondent, downloaded from http://www.globes.co.il/serveen/globes/docview.asp?did=1000769176&fid=1725.
(Continued)

*Primary Examiner* — Nicole F Lavert
(74) *Attorney, Agent, or Firm* — Fay Sharpe LLP

(57) ABSTRACT

The present disclosure describes systems, methods, devices for performing thought-controlled neuromuscular stimulation. Also described are methods for producing a neuromuscular stimulation cuff. The systems and methods generally relate to receiving and processing thought signals indicative of an intended action, and then delivering stimulation to effectuate the intended action through a neuromuscular stimulation cuff. The neuromuscular stimulation cuff includes a flexible printed circuit board having at least one finger and a plurality of electrogel discs disposed on the at least one finger. The neuromuscular stimulation cuff may be produced by providing a layer of polyimide, etching a conductive copper circuit including a plurality of electrodes into the layer of polyimide to form an etched circuit layer, adhering a cover layer onto the etched circuit layer to form a flexible printed circuit board (PCB), and cutting at least one finger from the flexible PCB. The neuromuscular stimulation cuff employs a flexible multi-electrode design which
(Continued)

allows for reanimation of complex muscle movements in a patient, including individual finger movement.

23 Claims, 20 Drawing Sheets

Related U.S. Application Data division of application No. 14/649,025, filed as application No. PCT/US2013/073247 on Dec. 5, 2013, now Pat. No. 9,884,178.

(60) Provisional application No. 61/734,150, filed on Dec. 6, 2012, provisional application No. 61/733,736, filed on Dec. 5, 2012.

(51) Int. Cl.
*A61N 1/36* (2006.01)
*H05K 3/10* (2006.01)

(52) U.S. Cl.
CPC ....... *A61N 1/0476* (2013.01); *A61N 1/36031* (2017.08); *A61N 1/36034* (2017.08); *H05K 3/10* (2013.01); *A61N 1/0492* (2013.01); *A61N 1/36003* (2013.01)

(56) References Cited

U.S. PATENT DOCUMENTS

| 2006/0253167 | A1 | 11/2006 | Kurtz et al. | |
|---|---|---|---|---|
| 2008/0215128 | A1* | 9/2008 | Rainey | A61N 1/0452 607/152 |
| 2010/0198044 | A1* | 8/2010 | Gehman | A61B 5/0408 600/393 |
| 2011/0021943 | A1 | 1/2011 | Lacour et al. | |
| 2011/0054286 | A1* | 3/2011 | Crosby | A61B 5/04085 600/372 |
| 2012/0316624 | A1 | 12/2012 | Smith | |

OTHER PUBLICATIONS

Garrett et al., "Problem 6: Neural Decoding and Modulation in Patients with Tetraplegia", Presentation by Chad Bouton of Battelle Memorial Institute.

Humber et al., "Nonsmooth Formulation of the Support Vector Machine for a Neural Decoding Problem", arXiv:1012.0958v1 [math.OC] Dec. 5, 2010.

Pasley et al., "Reconstructing Speech from Human Auditory Cortex", PLoS Biology, www.plosbiuology.org, Jan. 2012, vol. 10, Issue 1, e1001251.

Sweeney et al., "Neuromuscular stimulation selectivity of multiple-contact nerve cuff electrode arrays", Med. & Biol. Eng. & Comput., 1995, 33, 418-425.

International Search Report and Written Opinion dated Jun. 27, 2014, issued in PCT/US2013/073247 (from which this application claims priority).

* cited by examiner

SYSTEMS INCLUDING NEUROMUSCULAR STIMULATION CUFF

CROSS-REFERENCE TO RELATED APPLICATIONS

This application is a continuation of U.S. patent application Ser. No. 15/872,272, filed on Jan. 16, 2018 and since issued as U.S. Pat. No. 10,293,151 on May 21, 2019, which is a divisional of U.S. patent application Ser. No. 14/649,025, filed on Jun. 2, 2015, now U.S. Pat. No. 9,884,178, which issued on Feb. 6, 2018, which was a 371 of PCT Application No. PCT/US2013/073247, filed Dec. 5, 2013, which claimed priority to U.S. Provisional Patent Application Ser. No. 61/733,736, filed on Dec. 5, 2012, and to U.S. Provisional Patent Application Ser. No. 61/734,150, filed on Dec. 6, 2012, which are incorporated herein by reference in its entirety.

BACKGROUND

The present disclosure relates to systems, methods, and devices for thought-controlled neuromuscular stimulation. Generally, the system may be used to receive thought signals indicative of an intended action and provide electrical stimulation to a damaged or degenerated neuromuscular region to effectuate the intended action. Methods to produce a flexible neuromuscular stimulation cuff are also disclosed. The device may be a neuromuscular stimulation cuff which delivers stimulation to restore movement to parts of the body not under volitional control due to damaged or degenerated neural pathways from spinal cord injury, stroke, nerve damage, motor neural disease, and other conditions or injuries. The system can also be used in a patient that has some local neural or muscle degeneration for therapeutic or rehabilitation purposes.

Subcutaneous implantable neurostimulation cuffs have been commonly used to block pain and to restore function to damaged or degenerative neural pathways. These implantable cuffs are wrapped around a target nerve and generally include one or more electrodes arranged to stimulate the nerve. By including more than one electrode and/or a different geometry of electrodes, implantable cuffs such as the flat interface nerve electrode (FINE) have been able to achieve stimulation selectivity at the level of individual nerve vesicles.

Transcutaneous neurostimulation cuffs behave similarly to implantable cuffs, however there are important differences. Because the electrodes are placed against the skin, rather than through it, stimulation is preferably performed on skeletal muscle tissue or muscle groups, rather than peripheral nerves located deeper under the skin. Muscular stimulation may be preferable to stimulating major peripheral nerves, e.g. ulnar, median, radial nerves, as stimulating these nerves may cause a patient to feel a tingling sensation. By increasing the number and layout of electrodes in a neuromuscular cuff, similar to the direction taken with implanted nerve cuff designs, current generation neuromuscular stimulation cuffs have been able to selectively stimulate individual muscles or muscle groups.

Flexible transcutaneous cuffs have been developed which fit around a human appendage such as a forearm to control the wrist or fingers. These flexible cuffs may include sensors which record muscle activity, or EMG signals, and stimulate in response to the EMG signals. Thin film technologies have also become important in the development of functional electrostimulation (FES) devices. Devices incorporating thin film technology are often based on a polyimide substrate covered by a chromium, gold, or platinum film.

Current neuromuscular cuffs present many limitations, for example, their inability to receive a stimulation signal which is directly processed from thought signals. These neuromuscular cuffs are also not flexibly positioned over multiple stimulation points. Flexible electrode positioning is desirable when attempting to restore complex muscular movements through neuromuscular stimulation. Current neuromuscular cuffs are also incapable of accommodating a wide range of patient appendage geometries, e.g. varying circumferences, while also staying well adhered to the skin.

An effective wireless system for transmitting human brain signals directly to muscles, and thereby enabling movement through thought-control, has not yet been developed. Neuromuscular stimulation cuffs for such a system, e.g. which receive an input consisting of encoded "thought" signals and provide stimulation to muscular regions according to the signals, have also not been developed.

BRIEF DESCRIPTION

The present disclosure relates to systems, methods, and devices for thought-controlled neuromuscular stimulation. Included is a neuromuscular stimulation cuff which receives a thought signal indicative of an intended action, and in response, stimulates a damaged neuromuscular region to effectuate the intended action. The neuromuscular cuff may include a flexible design, e.g., including a plurality of electrodes arranged on flexible fingers across a single conductive layer. The flexible fingers allow for variable sized neuromuscular regions, e.g. paralyzed limbs, to fit within the neuromuscular cuff. The fingers may also allow for increased electrode positioning choices for reanimation of complex muscle movements. The neuromuscular cuff may further include an array of electrogel discs which provide enhanced electrical contact as well as keep cuff adhered to the skin during stimulation-induced movement.

In some embodiments, a system for thought-controlled neuromuscular stimulation includes a sensor for monitoring or recording neural signals from a patient, a neural signal processor for receiving the neural signals and processing the neural signals into a re-encoded signal, and a neuromuscular stimulation cuff for delivering stimulation to the patient according to the re-encoded signal.

In other embodiments, a method for thought-controlled neuromuscular stimulation includes receiving neurological signals from a patient indicative of an intended action, processing neurological signals, generating a re-encoded signal, and delivering neuromuscular stimulation to the patient according to the re-encoded signal to effectuate the intended action.

In yet other embodiments, a device for neuromuscular stimulation includes a flexible printed circuit board having at least one finger and a plurality of electrogel discs disposed on the at least one finger.

In additional different embodiments, a method for producing a neuromuscular cuff includes providing a layer of polyimide, etching a conductive copper circuit including a plurality of electrodes into the layer of polyimide to form an etched circuit layer, adhering a cover layer onto the etched circuit layer to form a flexible printed circuit board (PCB), and cutting at least one finger from the flexible PCB.

BRIEF DESCRIPTION OF THE DRAWINGS

The following is a brief description of the drawings, which are presented for the purposes of illustrating the exemplary embodiments disclosed herein and not for the purposes of limiting the same.

DETAILED DESCRIPTION

Figure 1:
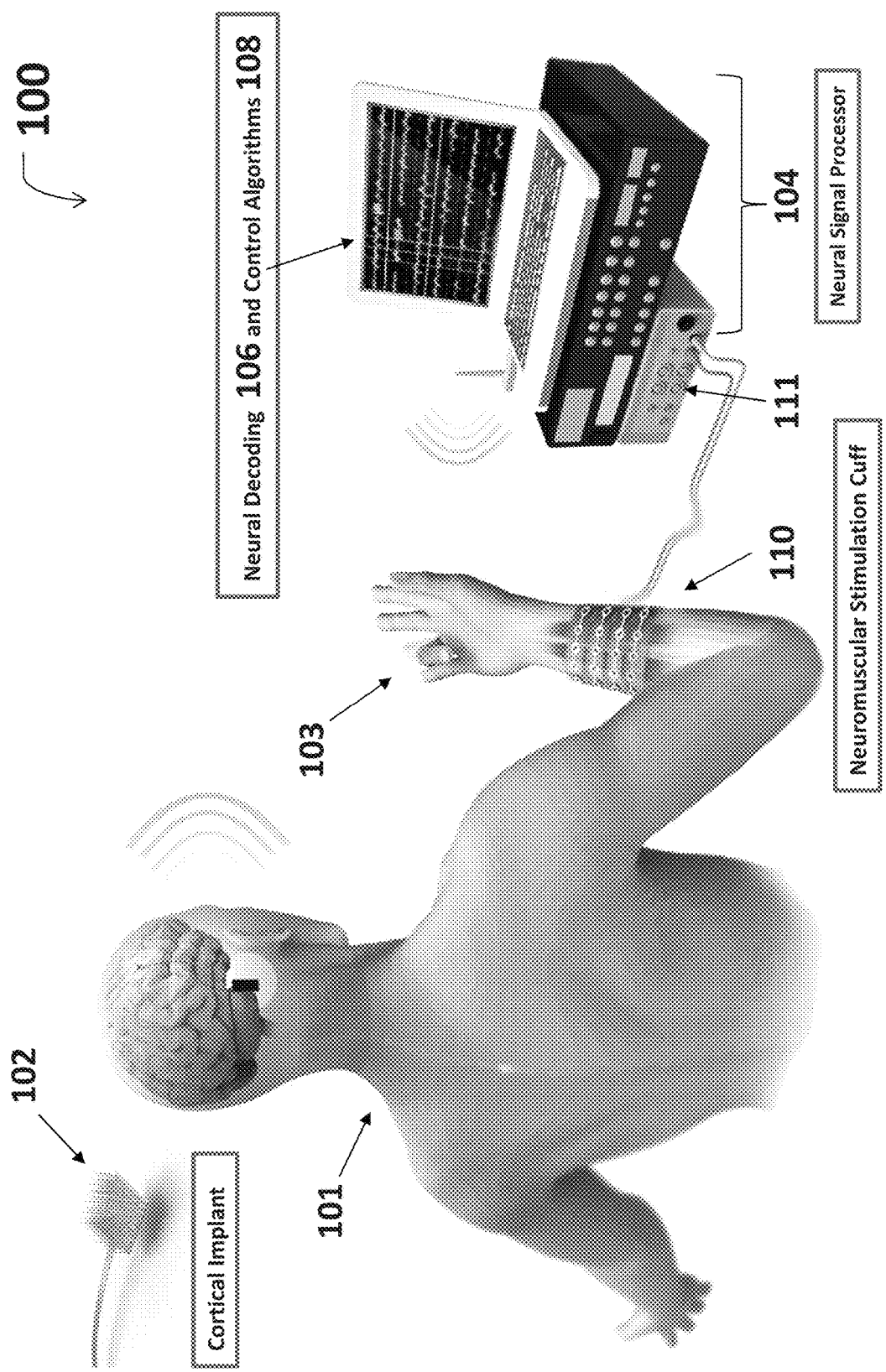
FIG. 1 is an overview diagram of one embodiment of a system for thought-controlled neuromuscular stimulation.

A more complete understanding of the processes and apparatuses disclosed herein can be obtained by reference to the accompanying drawings. These figures are merely schematic representations based on convenience and the ease of demonstrating the existing art and/or the present development, and are, therefore, not intended to indicate relative size and dimensions of the assemblies or components thereof.

Although specific terms are used in the following description for the sake of clarity, these terms are intended to refer only to the particular structure of the embodiments selected for illustration in the drawings and are not intended to define or limit the scope of the disclosure. In the drawings and the following description below, it is to be understood that like numeric designations refer to components of like function.

Figure 2:
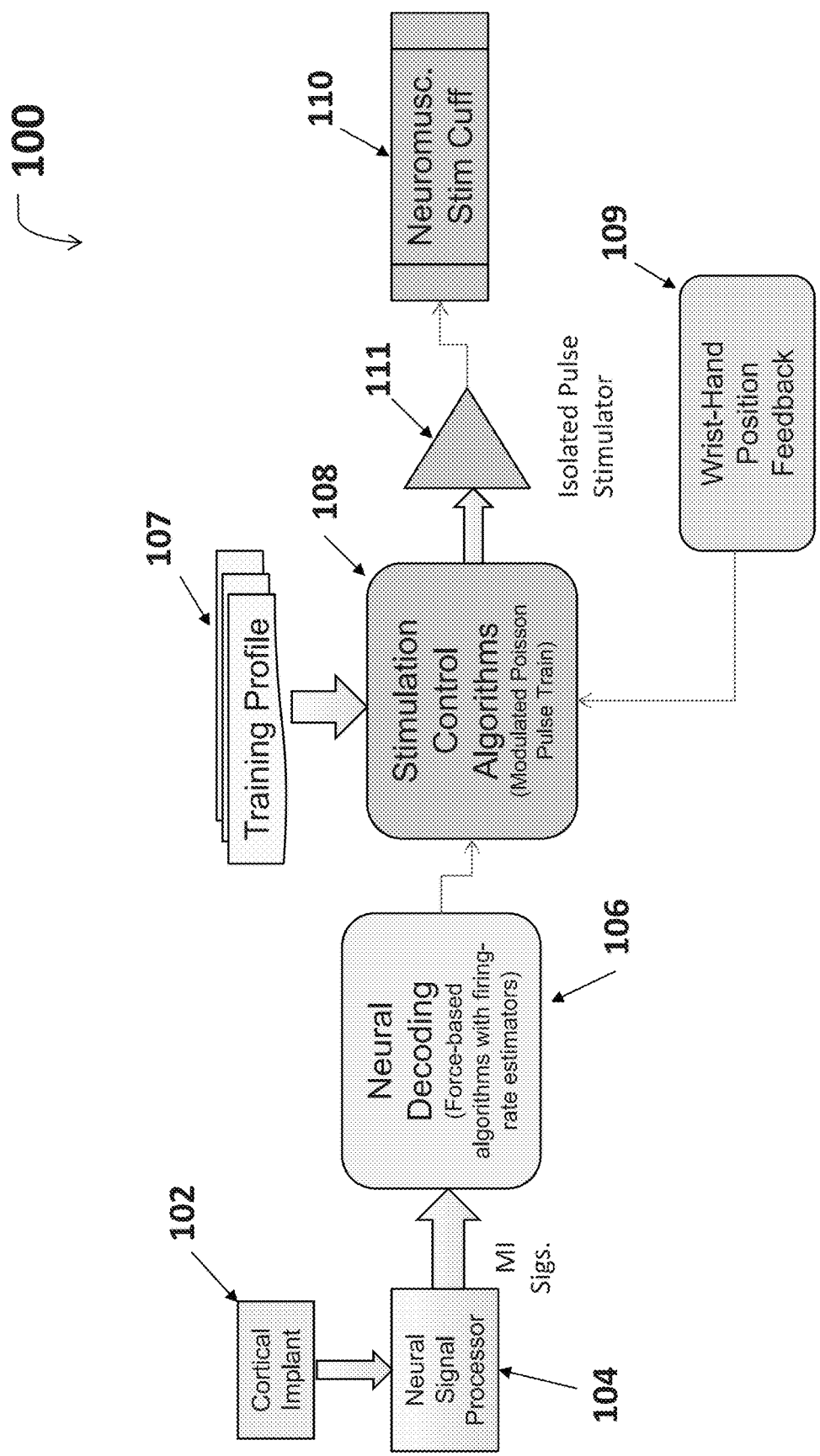
FIG. 2 is a block diagram for the decoding and re-encoding architecture operating within the system of FIG. 1.

With reference to FIG. 1 and FIG. 2, a system for thought-controlled neuromuscular stimulation may include a cortical implant 102 implanted into the cerebral cortex region of the brain. The cortical implant 102 in one embodiment includes a microelectrode sensing array, as depicted in FIG. 1. The microelectrode sensing array includes multiple channels (e.g. 96 channels) and may be wired to an amplifier which further amplifies signals received by the microelectrode array. The cortical implant 102 records "brain waves," more particularly neural signals which are representative of a varied set of mental activities. Neural signals include electrical signals produced by neural activity in the nervous system including action potentials, multi-unit activity, local field potential, ECoG, and EEG. These neural signals are sent wirelessly or, alternatively, through a wired connection, from the cortical implant 102 to a receiver on a neural signal processor device 104 for processing of the neural signals. In another embodiment, a scalp based interface, headset, or other sensor 102 picks up electroencephalogram (EEG) signals and sends them to the receiver on the neural signal processor device 104.

The neural signal processor 104 may include a processor including neural decoding algorithms 106 and/or control algorithms 108. These algorithms 106, 108 allow for a received neural signal input to be decoded and subsequently re-encoded for use in neuromuscular stimulation. For example, a received neural signal may be isolated to predict arm and/or hand movements a patient is thinking about. The neural signal processor 104 may also include an oscilloscope or other signal waveform viewing and/or manipulation device. The neural signal processor also preferably includes an isolated pulse stimulator 111 which receives a processed signal and generates a pulse signal for use in neuromuscular stimulation by an attached neuromuscular stimulation cuff 110.

With reference to FIG. 2, the system for thought control at a more complex architectural level includes the cortical implant or sensor 102 and the neural signal processor 104 which allow for the recording of neural signals and the initial processing of the signals, respectively. Initial signal processing may include analog to digital conversion, normalization, and/or other filtering and processing methods known by one having ordinary skill in the art. Initially processed signals are then decoded by the neural decoding algorithms 106. In exemplary embodiments, the neural decoding algorithms 106 include force-based algorithms with firing-rate estimators.

The decoded signal output of the neural decoding algorithms 106 is further processed by the stimulation control algorithms 108. In exemplary embodiments, the stimulation control algorithms 108 produce an output of peak current amplitude modulated, pulse width modulated, or frequency modulated pulse trains going to the cuff electrodes. The pulse train can also be a non-stationary Poisson type train where average pulse rate (frequency) is modulated. This may help reduce muscle fatigue as it more closely matches to the body's natural nervous system. An example of using poisson-distributed impulse trains to characterize neurons in a region of the brain is disclosed in Pienkowski et al., Wiener-Volterra Characterization of Neurons in Primary Auditory Cortex Using Poisson-Distributed Impulse Train Inputs, J. Neurophysiology (March 2009). Stimulation control algorithms 108 may be altered through input received from a training profile 107. The training profile 107 may include training profile data representative of past user training sessions, e.g. motion demonstrations or coaching periods. Training data may be used to alter and/or define simulation control algorithms 108 during signal processing. Incorporating training data into stimulation control algorithms 108 through a model-based approach yields more accurate decoding, e.g. patient thoughts accurately translated into a complex motion, than prior position-based decoding efforts have shown. Additionally or alternatively, wrist-hand position feedback 109 may be used to alter and/or define stimulation control algorithms 108 during signal processing.

Signal control algorithm 108 output may be sent to the isolated pulse generator 111, where the signal is converted into a waveform that is suitable for neurostimulation. Suitable waveforms may include monophasic and biphasic pulses with a voltage between 80 to 300 Volts. However, even higher voltages may be used as long as safe current levels are maintained and proper insulation is used. In exemplary embodiments, the waveform is a monophasic pulse with a peak current of 0-20 mA which is modulated to vary strength of muscle contraction, frequency of 50 Hz, and a pulse width duration of 500 ms. The output of the isolated pulse generator 111 is sent to the neuromuscular stimulation cuff 110 to deliver functional electrostimulation to the patient.

Figure 3:
FIG. 3 is a flow diagram for one embodiment of a method for providing thought-controlled neuromuscular stimulation.

With reference to the flow diagram set forth in FIG. 3, a method for providing thought-controlled neuromuscular stimulation S100 starts at S101. At S102 neurological signals are received from a patient indicative of an intended action. For example, neurological signals may be received through cortical implant 102. At S104 the neurological signals are processed, which may include analog to digital conversion or filtering. At S106, the digitized signals are decoded by at least one neural decoding algorithm 106. At S108, the decoded signals are processed by at least one stimulation control algorithm 108. At S110, the method alternatively includes altering the stimulation control algorithms 108 by training data which is stored in the training profile 107. At S112, the method alternatively includes altering the stimulation control algorithms 108 based on movement data, e.g. wrist-hand position feedback 109. At S114, the output of the at least one signal control algorithm 108 is converted into a re-encoded signal consisting of multiple pulse trains, each pulse train going to a corresponding electrode 114. At S114, neuromuscular stimulation is delivered to the patient by sending the re-encoded signal to the neuromuscular stimulation cuff 110.

In another embodiment, the method for providing thought-controlled neuromuscular stimulation S100 further includes at S117 delivering neuromuscular stimulation to the patient by selectively delivering stimulation to at least one pair of electrodes 114 within a neuromuscular cuff 110 to effectuate the intended action.

In yet another embodiment, the method S100 further includes S103 recording neurological signals from a patient. These neurological signals may be sensed from, e.g., a forearm or wrist region with neural pathway damage. Recording may also occur at a neurologically intact region such as a functional leg, for which stimulation pulses can be provided for stimulating commonly tied motions in damaged limbs, e.g. arms and legs. Commonly tied motions include hip and arm movements or pivoting movements. In the same embodiment, method S100 at S118 may further include delivering neuromuscular stimulation to the patient by selectively stimulating to at least one pair of electrodes within the neuromuscular cuff 110 based on the re-encoded signal.

Figure 4:
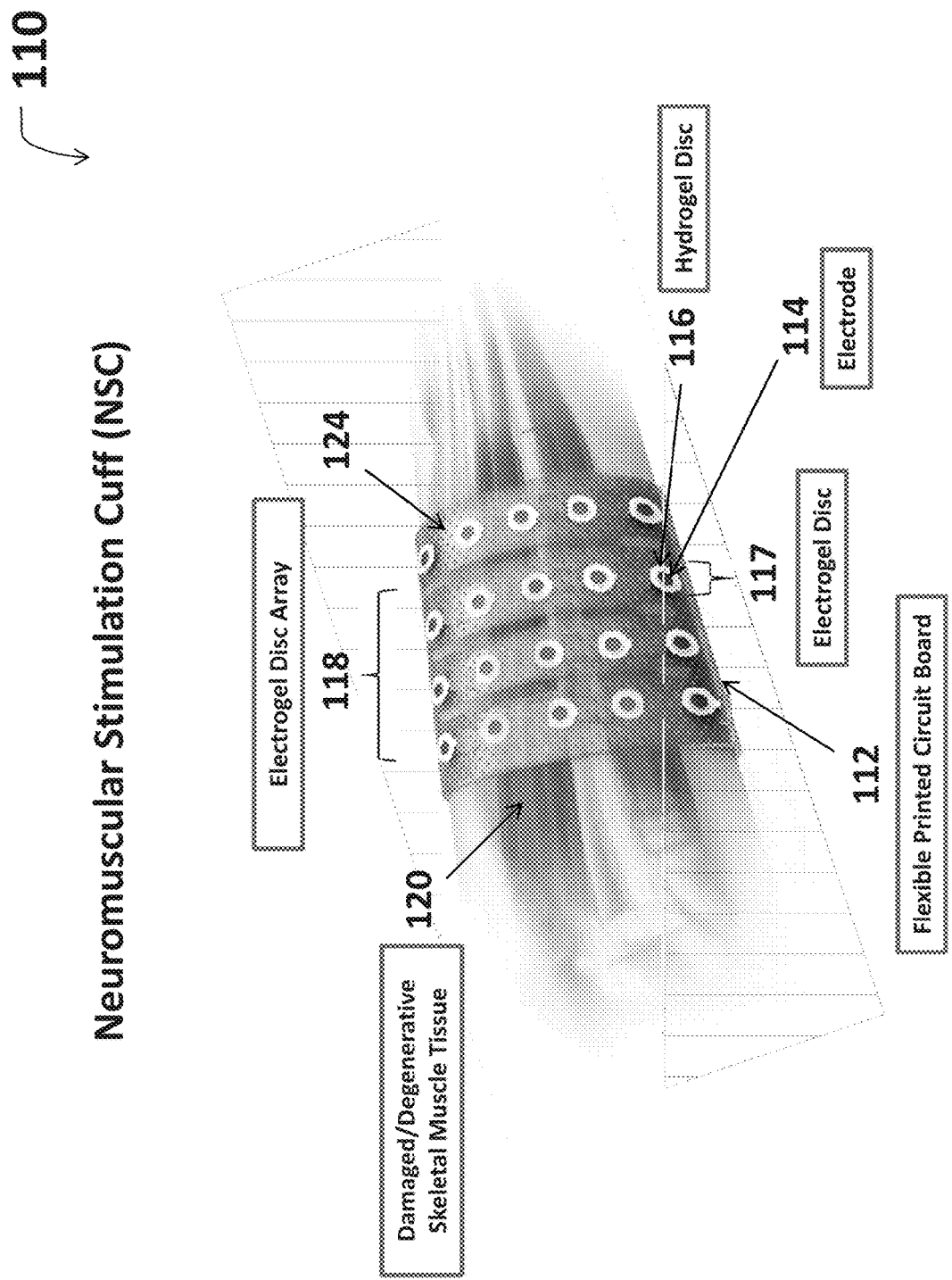
FIG. 4 is a perspective drawing of a neuromuscular stimulation cuff device according to an exemplary embodiment, shown in place on a human arm.

With reference to FIG. 4, an exemplary embodiment of the neuromuscular stimulation cuff 110 includes a flexible printed circuit board (PCB) 112 upon which electrodes 114 and hydrogel discs 116 are arranged in an electrogel disc array 118. The neuromuscular stimulation cuff 110 fits over a damaged or degenerative neuromuscular region 120, e.g. a patient's arm as illustrated. The flexible PCB 112 may be comprised of a single layer of flexible polyimide material. Up to approximately twenty electrodes 114 may be individually etched onto each finger 124 of the flexible PCB 112 as a copper layer. In exemplary embodiments, the flexible PCB 112 has a total of eighty electrodes 114 disposed over four fingers 124. The electrodes 114 may be subsequently plated with a conductive metal such as gold, palladium, or silver for greater conductivity.

In some embodiments, electrodes 114 both stimulate a neuromuscular region 120 by stimulating individual muscles and/or groups of muscles, as well as monitor or record skeletal muscle activity, specifically electromyography (EMG) signals. Sensed EMG data pertaining to a sensed muscle target may be used in methods for closed or open loop stimulation of the muscle target. Sensed EMG data may also be analyzed in deciding whether to reposition the neuromuscular stimulation cuff 110 within the neuromuscular region 120 or to turn off individual electrodes 114 within the electrogel disc array 118.

Hydrogel discs 116 may be rolled over the electrodes 114 to provide enhanced electrical and mechanical coupling. When appropriately aligned, the hydrogel discs 116 completely cover the electrodes 114 and effectively form conductive electrogel discs 117. Put another way, the electrodes are located between the base layer and the hydrogel discs. Electrical coupling is enhanced in that hydrogel provides greater conductive contact with the skin than is achievable with a bare metal-plated electrode surface. Additionally, a carrier signal provided to any of the electrogel discs 117 in the electrogel array 118 may conduct through the tissues of a patient and be released at any other electrogel disc 117 provided in the array 118. Enhanced mechanical coupling is provided through the exemplary adherence characteristics of hydrogel to the skin. Hydrogel discs 116 may stay coupled to the skin even during complex patient movement. The hydrogel discs are commercially available as a tape which may be rolled on an electrode surface. One such example includes AmGel 2550 from AmGel Technologies. In the exemplary embodiment of the neuromuscular cuff shown in FIG. 4, the hydrogel discs are provided through custom spaced hydrogel discs located on AmGel 2550 rolled hydrogel tape.

The electrogel disc array 118 is spread over a plurality of fingers 124, wherein the fingers 124 are cut from the flexible PCB 112 to provide additional flexibility in the placement of electrogel discs 117. Reanimation of complex motion may require stimulating muscles which are not located directly along the dimensions of a conventionally shaped neuromuscular cuff 110. By wrapping fingers 124 around different muscular regions, e.g. the lower wrist and thumb, complex motions such as thumb movement may be reanimated more effectively than with limited placement options.

Figure 5:
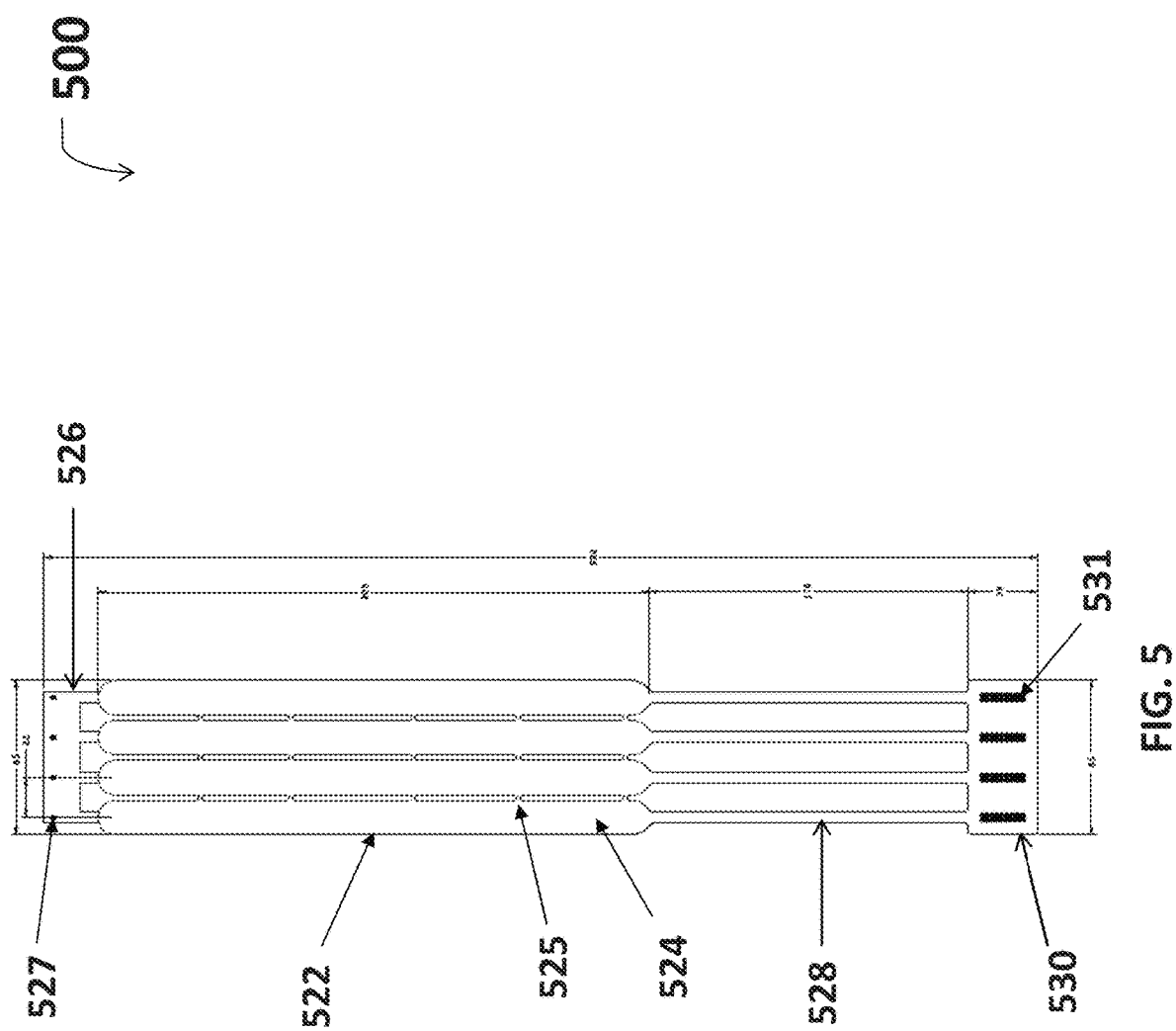
FIG. 5 is a diagram for a concept design for fabricating one embodiment of the neuromuscular stimulation cuff device.

FIGS. 5-11 are views of various layers of the neuromuscular stimulation cuff, and are separated for convenience and understanding. With reference to FIG. 5, one embodiment of the neuromuscular stimulation cuff device 110 may be fabricated in accordance with a concept design 500. Dimensions of and between the various components of the concept design 500 are indicated in millimeters (mm). The concept design 500 includes, as shown here, a single layer of polyimide base material 522. In some embodiments, the polyimide base material is a DuPont AP8523E polyimide which is 50 μm (micrometers) thick and rolled-annealed copper clad at 18 μm thick. This base material serves as a substrate for the other layers of the neuromuscular stimulation cuff. The base material 522 is cut into four fingers 524, where the electrodes will be located. The fingers can be attached to each other, for example by five webbings 525 which run between adjacent fingers. An optional fork 526 of polyimide material is located at one end of the fingers. The fork connects all of the fingers, and is provided for structural support for design and mounting. Drilled holes 527 are provided in the fork 526 for support and/or mounting purposes. In some embodiments, the four drilled holes 527 are approximately 2.387 mm in diameter with a tolerance of +/0.076 mm. Headers 528 extend from the end of each finger opposite that of the fork. These headers are thinner than the fingers and connect the fingers 524 to a rigidizer 530. Though not illustrated, webbings can also be provided between adjacent headers as well if desired. The rigidizer 530 is an inflexible circuit board used for interfacing with the neural signal processor 104. Drilled holes 531 are additionally located on the rigidizer 530 which represent connector pin insertion points. In exemplary embodiments, eighty drilled holes 531 are approximately 1.016 mm in diameter with a tolerance of +/−0.05 mm.

Figure 6:
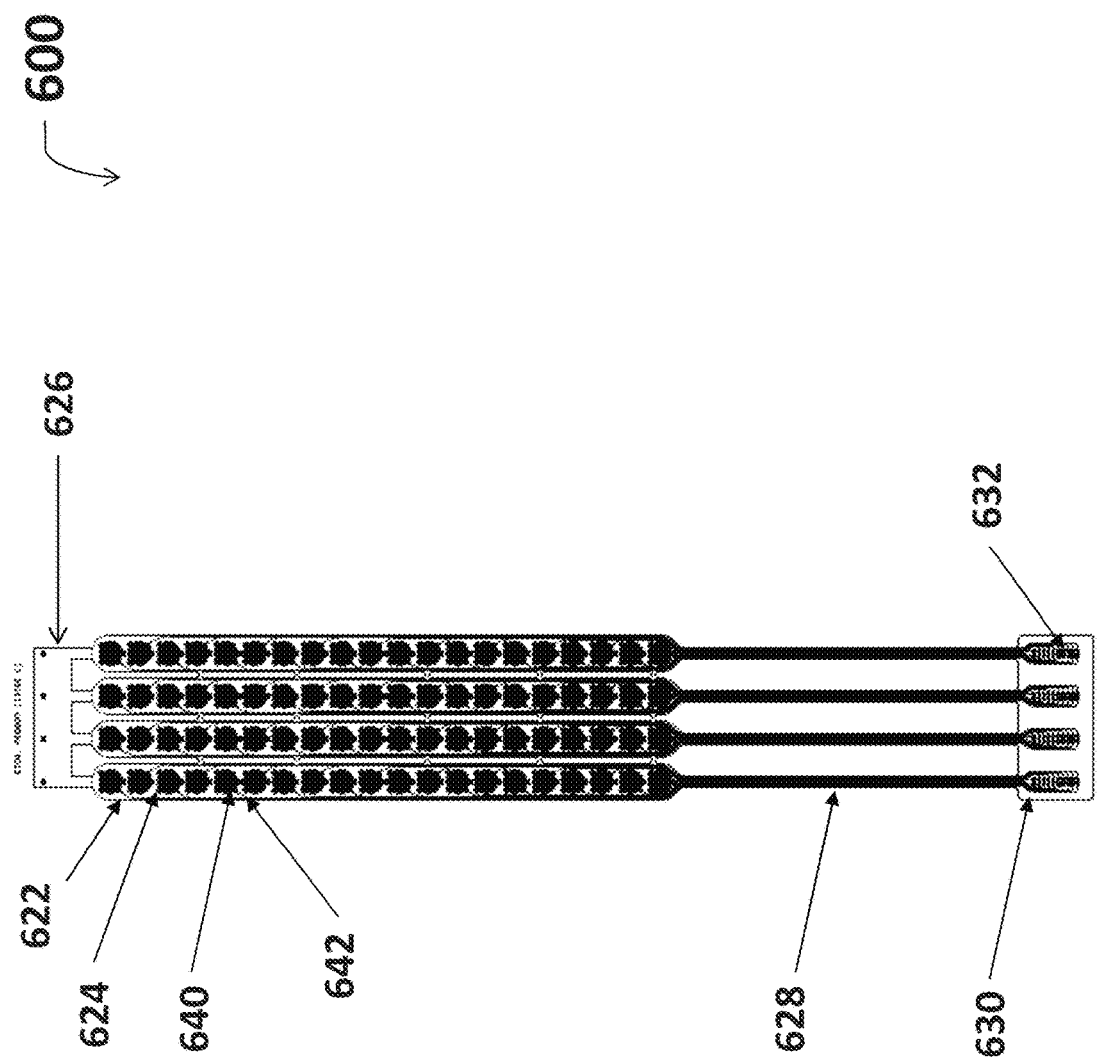
FIG. 6 is a diagram for an etched circuit layer for fabricating one embodiment of the neuromuscular stimulation cuff device.

With reference to FIG. 6, an etched circuit layer 600 for fabricating the neuromuscular stimulation cuff device 110 is shown. The etched circuit layer 600 is located on the surface of the polyimide substrate 622, upon which copper electrodes 640 and connective copper traces 642 are etched. The electrodes 640 and traces 642 run along the four fingers 624 of the substrate 622. The traces 642 run longitudinally down the four headers 628 to electrically connect the electrodes 642 to the rigidizer 630. The rigidizer 630 is an inflexible circuit board used for interfacing with the neural signal processor 104. The traces 642 continue onto rigidizer 630 and end, in this exemplary embodiment, at eighty connective points 632, which represents twenty connective points 632 per finger 624. Each of the eighty connective points 632 corresponds to an individual electrode 640, electrically connected through an individual trace 642.

Figure 7:
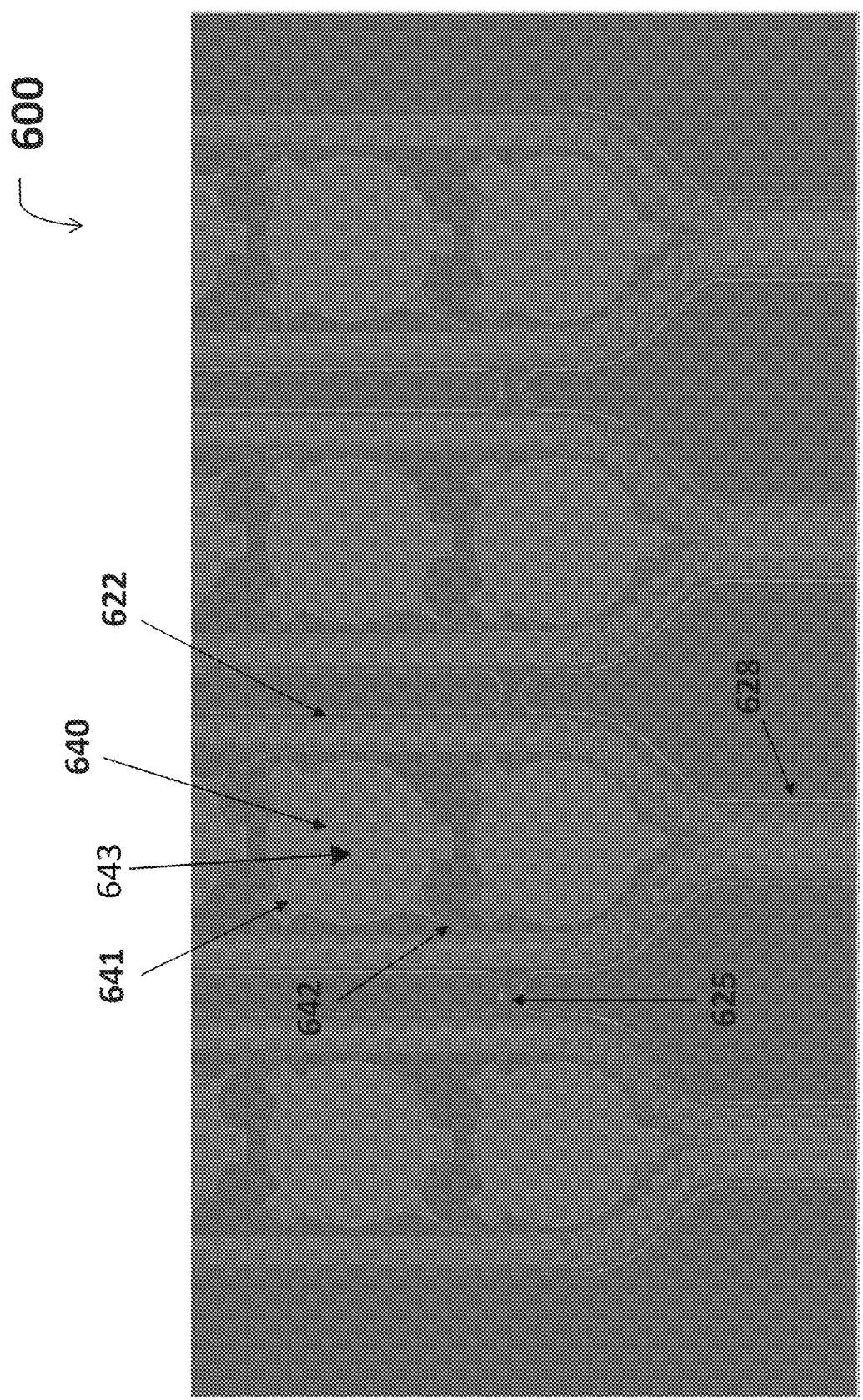
FIG. 7 is a close-up view diagram of the etched circuit layer of FIG. 6.

FIG. 7 is a closer view of the etched circuit layer 600 of FIG. 6. The substrate 622, electrodes 640, and traces 642 are more particularly seen here. Each electrode 640 is individually connected to a single trace 642, and the trace 642 runs down header 628 to the rigidizer 630 (not shown). In some embodiments, the traces 642 are approximately 0.127 mm in width. As illustrated here, each electrode 640 includes at least one ear 641 which is used to support the electrode 640 upon the substrate 622. As seen here, each electrode includes a central area 643 and three ears 641. The central area has a circular shape and is used as an electrical contact. Each ear extends beyond the perimeter of the central area. As illustrated here, two ears are separated by 60 degrees, and are separated from the third ear by 150 degrees.

Figure 8:
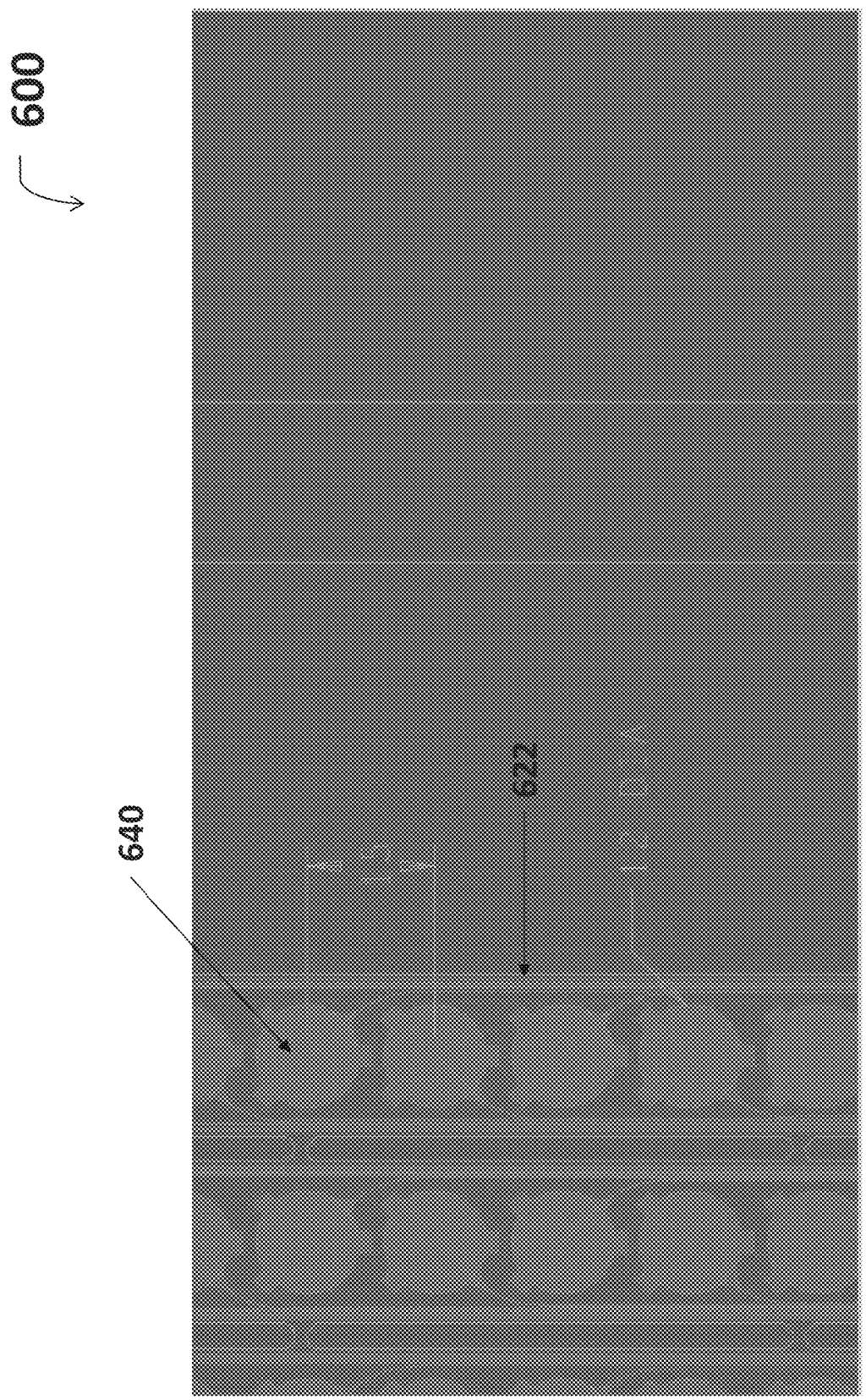
FIG. 8 is an alternative close-up view diagram of the etched circuit layer of FIG. 6.

Referring to FIG. 8, the etched circuit layer illustrated in FIG. 6 may include electrodes 640 that are approximately 12 mm in diameter (not counting the ear) and spaced 15 mm apart. This 15 mm spacing between electrodes would dictate the custom spacing required for subsequent application of hydrogel discs 114.

Figure 9:
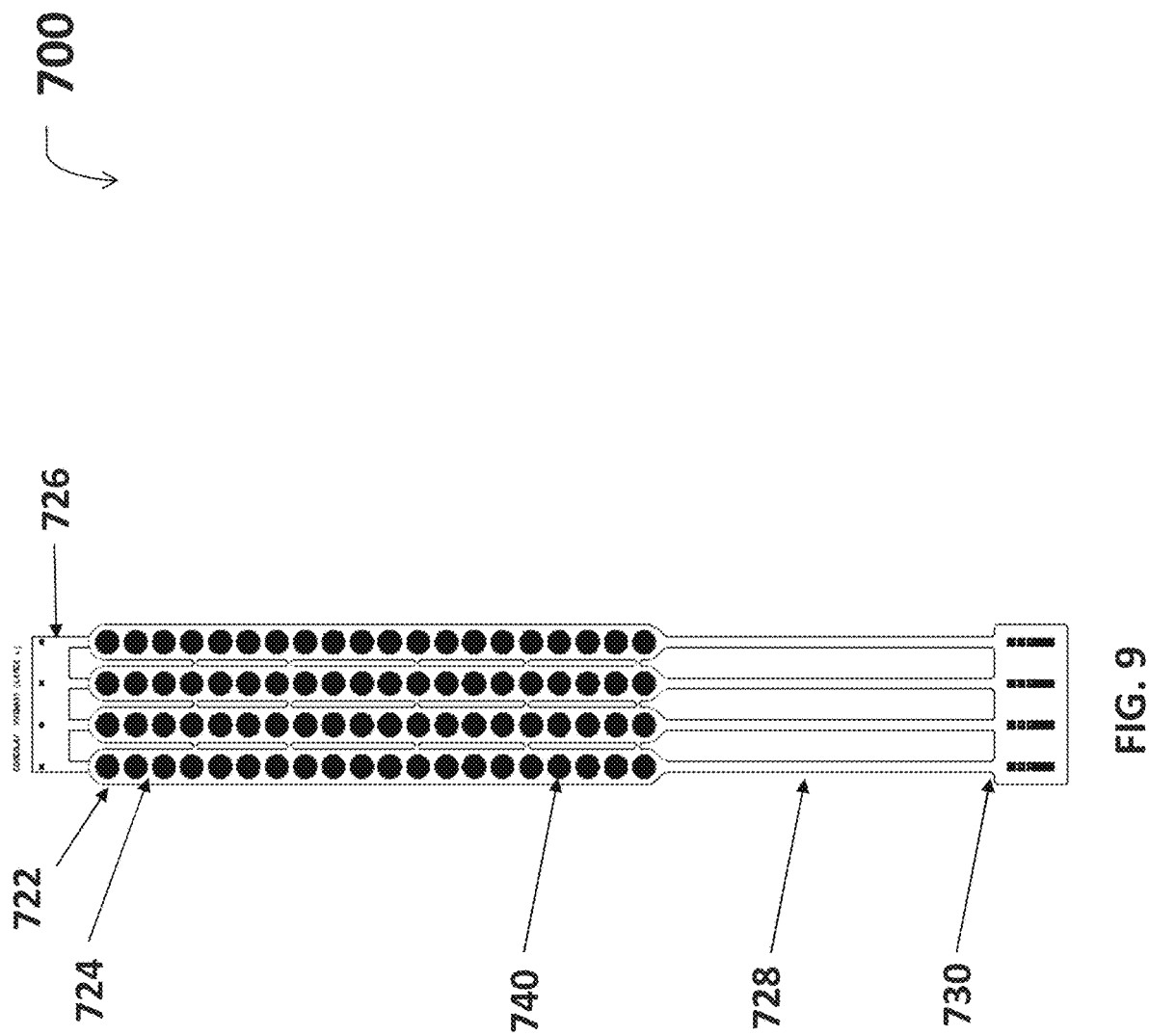
FIG. 9 is a diagram for a coverlay layer used in fabricating one embodiment of the neuromuscular stimulation cuff device.

FIG. 9 illustrates a coverlay layer 700 which would be placed over the electrodes and traces. The coverlay layer can be made from a single layer of polyimide 722, which is preferably thinner than the substrate upon which the electrodes and traces are copper-etched. In one embodiment, the coverlay layer is a DuPont LF0110 polyimide material which is a 25 μm thick coverfilm. A further thickness of 25 μm of acrylic adhesive can be used for adhering the coverlay layer 700 to the etched circuit layer 600. The coverlay layer includes a fork 726, fingers 724, headers 728, and rigidizer section 730 which corresponds to these areas on the base substrate 522 and the etched circuit layer 600. Cutouts 740 are left in the fingers to expose the central area of the electrodes, and on the rigidizer section 730 for the electrical connectors.

The coverlay layer 700, when applied over the etched circuit layer 600, covers the copper traces 642 etched on the fingers 724 and the headers 728. The coverlay layer 700 does not cover the central area 643 of the electrodes, but does cover the ears 641, thus fixing the electrodes in place between the substrate and the coverlay layer. In addition, the electrical connectors in the rigidizer section 730 will remain uncovered. The exposed central area of the electrodes 640 are preferably plated with a conductive metal such as tin, platinum, or gold. In one embodiment, exposed copper electrodes are plated with electroless-nickel-immersion-gold (ENIG) at the level of 3-8 ul gold over 100-150 ul nickel.

Figure 10:
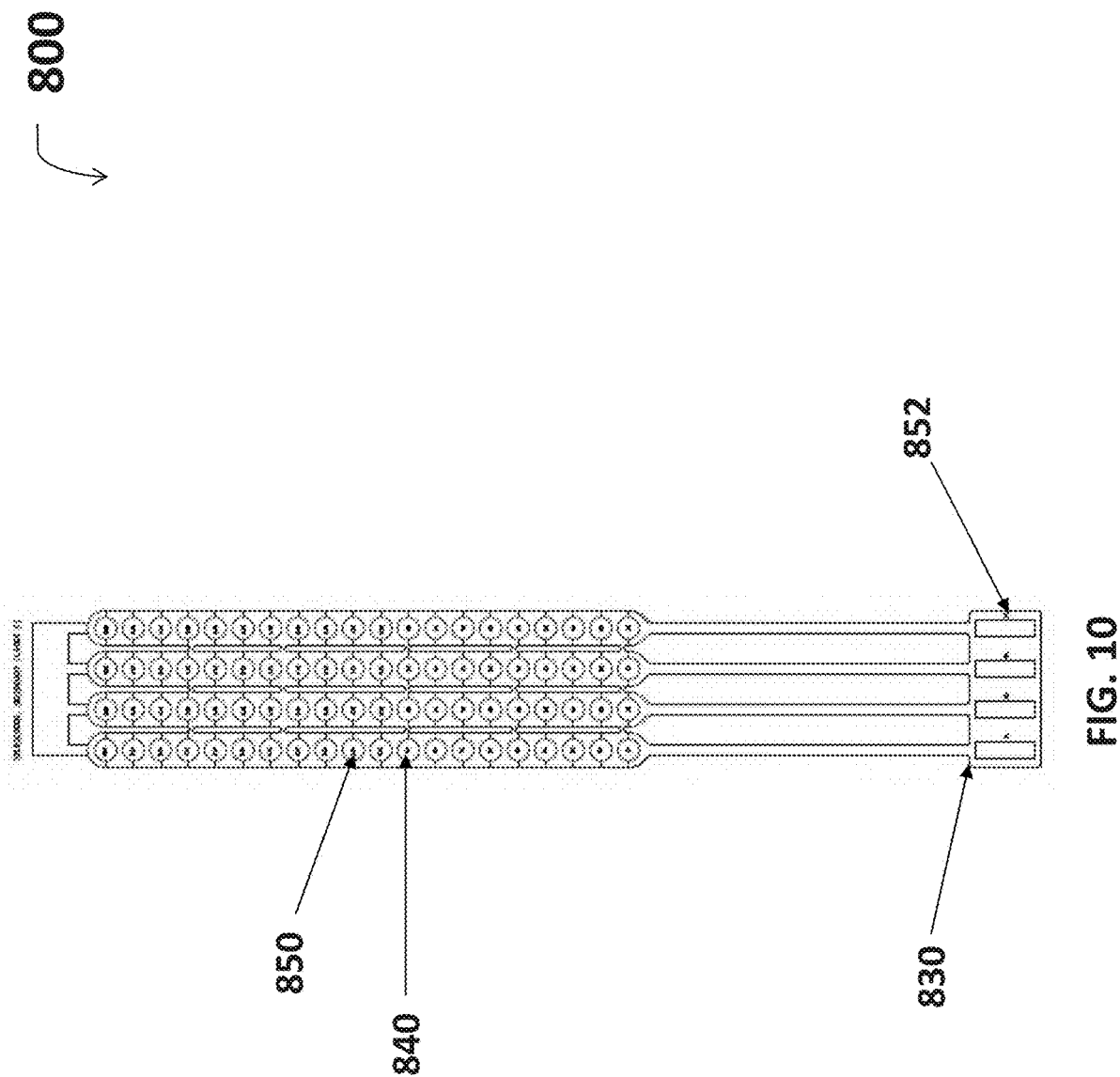
FIG. 10 is a diagram for a silkscreen layer used in fabricating one embodiment of the neuromuscular stimulation cuff device.

FIG. 10 is a diagram for a silkscreen layer 800 that can be used in fabricating the neuromuscular stimulation cuff device 110. The silkscreen layer 800 is applied to the combination of the etched circuit layer 600 and coverlay layer 700 to identify individual electronic elements. A first silkscreen identification number 850 is provided to each electrode 840 so that it may be more easily found after visual inspection. In one embodiment, first silkscreen identification numbers 850 span from A1-A20 and D1-D20 to represent eighty individual electrodes 840. A second silkscreen identification number 852 identifies the connection ports for a rigidizer 830. In one embodiment, second silkscreen identification numbers 852 span from J1-J4. Both first and second silkscreen identification numbers 850, 852 are provided on a secondary side of the neuromuscular stimulation cuff 110, or side facing away from exposed electrodes 740. In an exemplary embodiment, silkscreen identification numbers 850, 852 are provided by white epoxy nonconductive ink.

Figure 11:
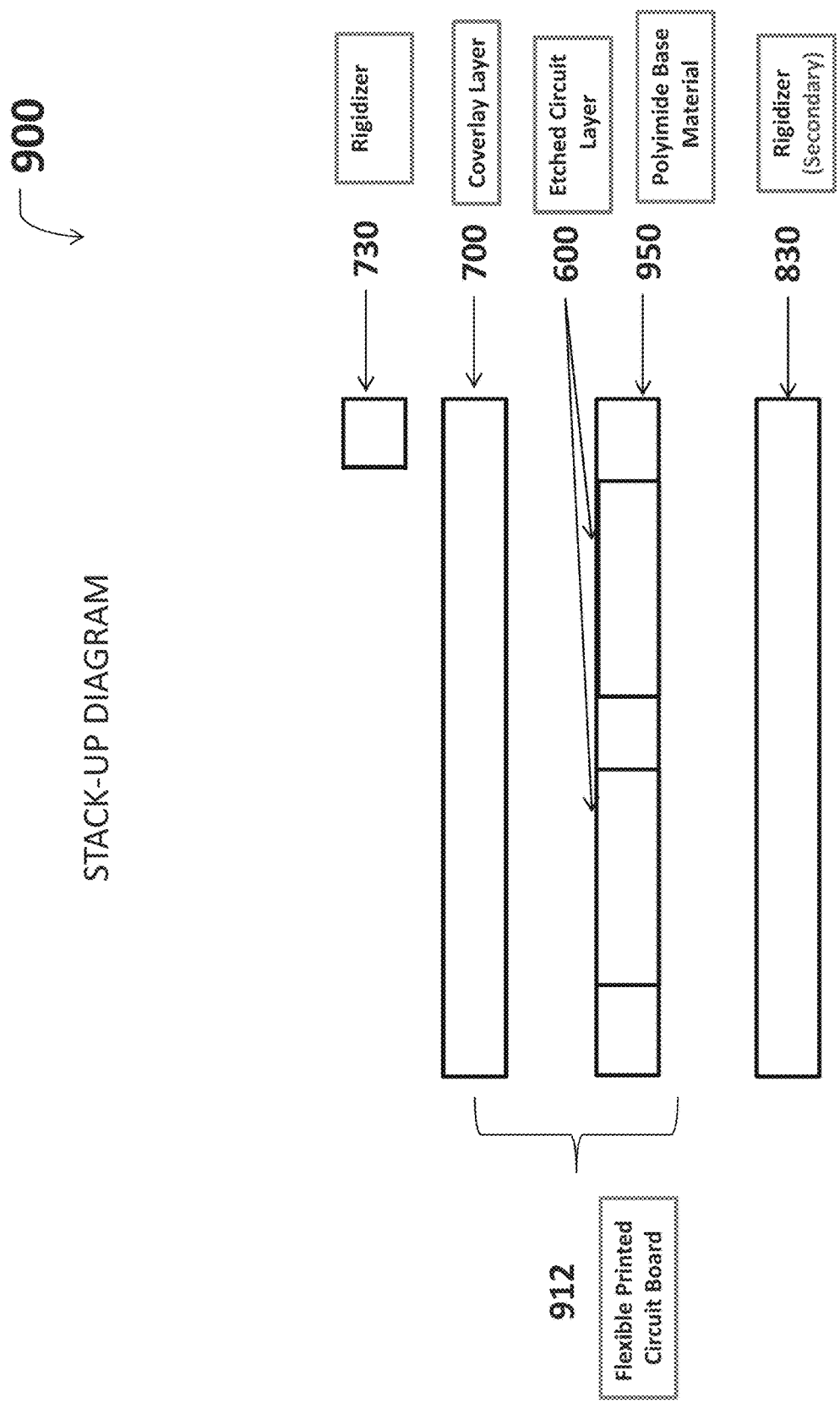
FIG. 11 is a stack-up diagram used in fabricating one embodiment of the neuromuscular stimulation cuff device.

Referring now to FIG. 11, various embodiments of the neuromuscular stimulation cuff device may be fabricated according to stack-up diagram 900. A polyimide base material provides a substrate 950 upon which various components are fixed. A secondary side rigidizer 830 is laminated to a secondary surface of the substrate 950. The etched circuit layer 600 is fabricated onto a primary surface of the substrate (opposite the secondary surface), and includes electrodes and traces. The coverlay layer 700 is subsequently adhered to the etched circuit layer 600 which covers the traces and leaves exposed portions of the electrodes. The combination of the substrate 950, etched circuit layer 600, and coverlay layer 700 is defined as the flexible PCB 912. Primary rigidizer 730 is stacked upon the coverlay layer to complete the electrical connection required to interface the flexible PCB with the neural signal processor 104.

Figure 12:
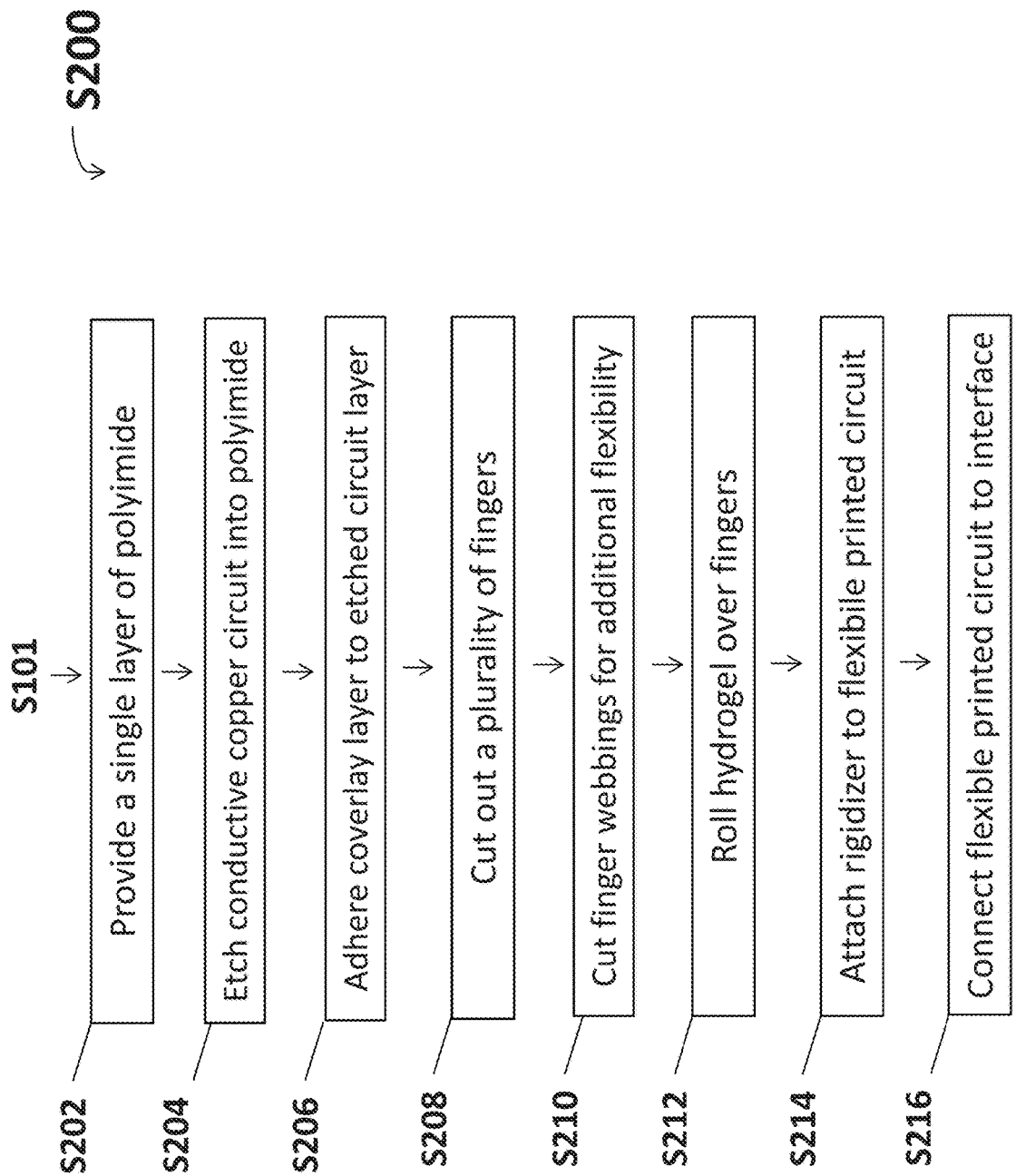
FIG. 12 is a flow diagram for one embodiment of a method for producing a neuromuscular cuff.

With reference to the flow diagram set forth in FIG. 12, one embodiment of a method for producing a neuromuscular cuff S200 starts at S201. At S202 a single layer of polyimide base material 950 is provided. At S204, an etched circuit layer is fabricated onto the polyimide base material 950 by etching a conductive copper circuit into the polyimide. At S206 a polyimide coverlay layer 700 is adhered to the etched circuit layer 600. Adhering the coverlay layer 700 to the etched circuit layer 600 completes the formation of the flexible PCB 912. At S208, a plurality of fingers 724 may optionally be cut from the flexible PCB 912 to provide additional contact points for stimulation of muscles or sensing EMG signals. At S210, finger webbings 725 may optionally be cut from the flexible PCB 912 to separate the fingers 724 and provide additional flexibility, such as to accommodate limb twisting (such as the forearm) while maintaining contact. At S212, hydrogel may optionally be rolled over fingers 724 to with electrodes create electrogel discs 117. At S214, a rigidizer 630, 730, 830 is attached to the flexible PCB 912 for interfacing with the neural signal processor 104. At S216, the flexible PCB 912 is interfaced with the neural signal processor 104.

Figure 13:
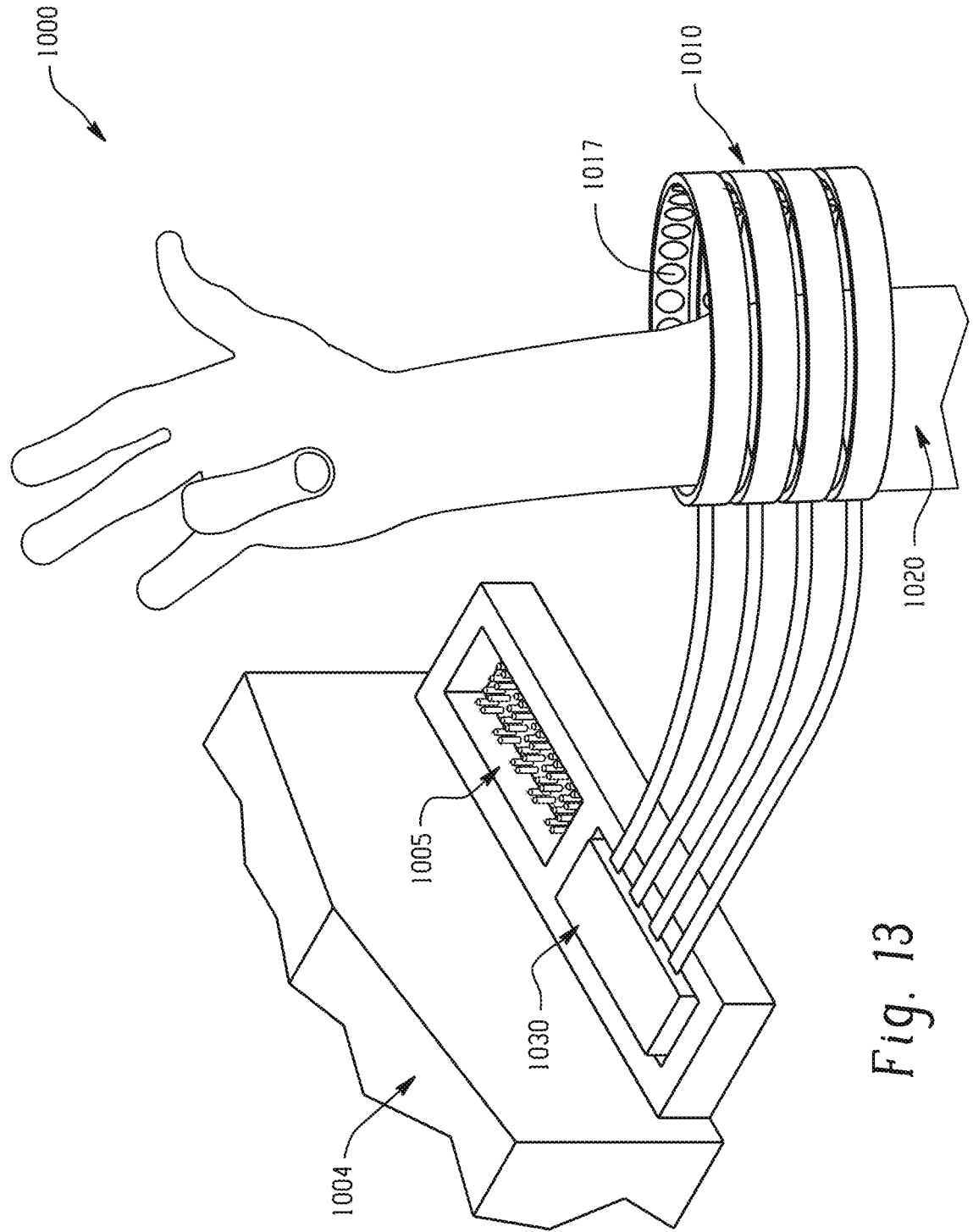
FIG. 13 is an exemplary photograph showing individual finger movement within a system for thought-controlled neuromuscular stimulation.

With reference to FIG. 13, individual finger movement within a system for thought-controlled neuromuscular stimulation 1000 is demonstrated. A neuromuscular cuff 1010 according to one embodiment is wrapped over a damaged or degenerative neuromuscular region 1020. The neuromuscular cuff 1010 is interfaced with a neurological signal processor 1004 through attached rigidizer 1030. The rigidizer is attached to a connection port 1005 on the neural signal processor 1004. Received neurological signals indicative of patient thinking about moving their first two digits has been decoded and re-encoded into pulse train signals transmitted to various electrodes on the neuromuscular stimulation cuff 1010. Using a specific number and spacing of electrodes/electrogel discs 1014, 1017 in neuromuscular stimulation cuff 1010 has allowed for high resolution and non-invasive neuromuscular stimulation which effectuates the intention of the patient.

Electrogel discs 1017 operate in pairs when reanimating motion. Individual digit movement may be effectuated through the operation of two to three pairs (4 to 6 units) of electrogel discs 1017 which are stimulating in tandem. Selecting particular pairs of electrogel discs 1017 to reanimate motion as indicated by a decoded brain signal is advantageously performed by the neuromuscular stimulation cuff 1010, as each electrogel disc 1017 is connected to the neurological signal processor 1004 individually along a single trace etched into a conductive layer of flexible polyimide material.

Figure 14:
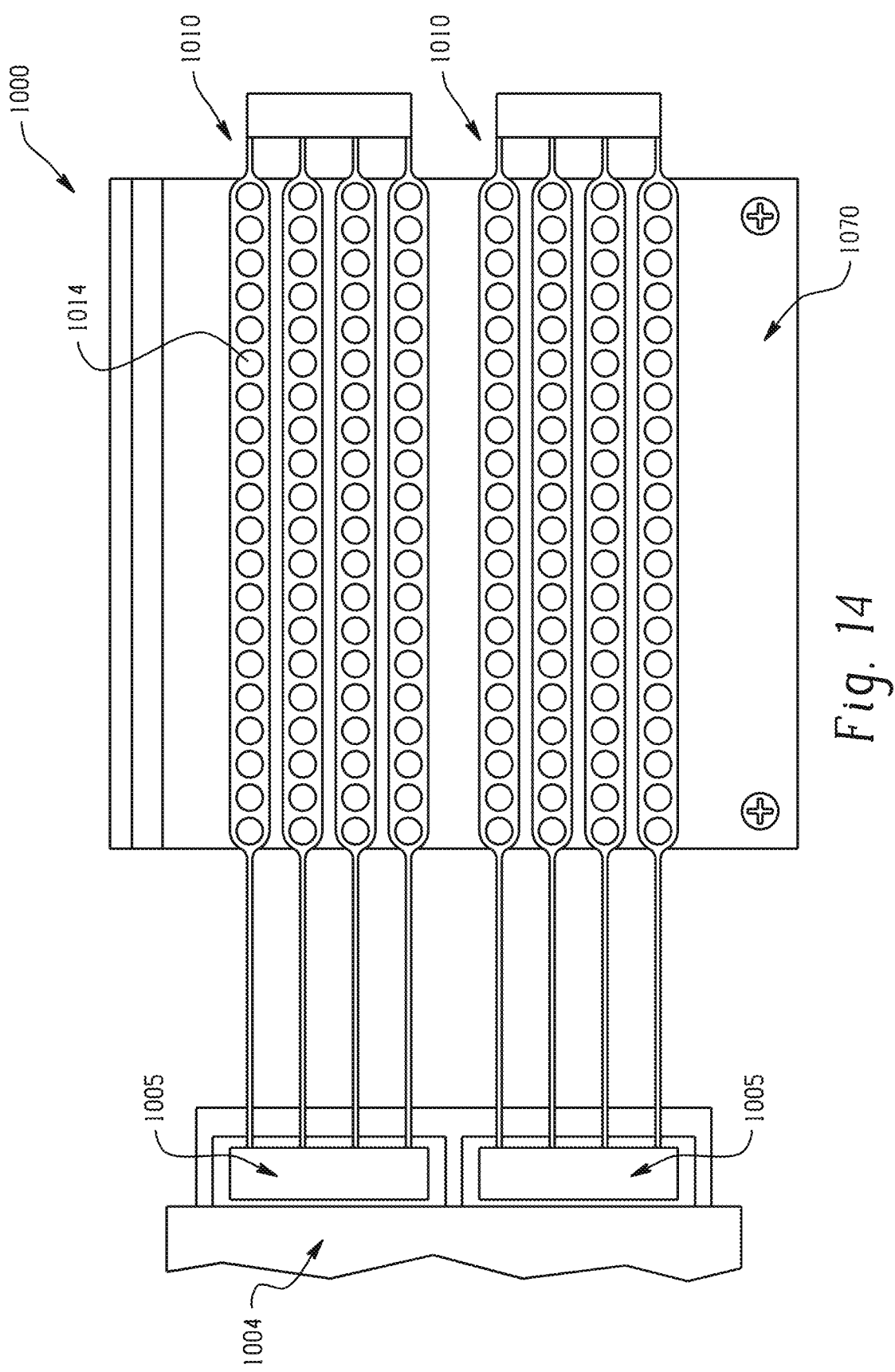
FIG. 14 is an exemplary photograph showing two neuromuscular cuff devices according to one embodiment disposed on a preparation bench.

With reference to FIG. 14, two neuromuscular cuff devices 1010 according to one embodiment are disposed on a preparation bench 1070. The preparation bench 1070 may be used to keep cuff devices 1010 flat and roll hydrogel tape across electrodes 1016. Properly adhered hydrogel discs 116 (not shown) should fully cover the surface of electrodes 1014.

Figure 15:
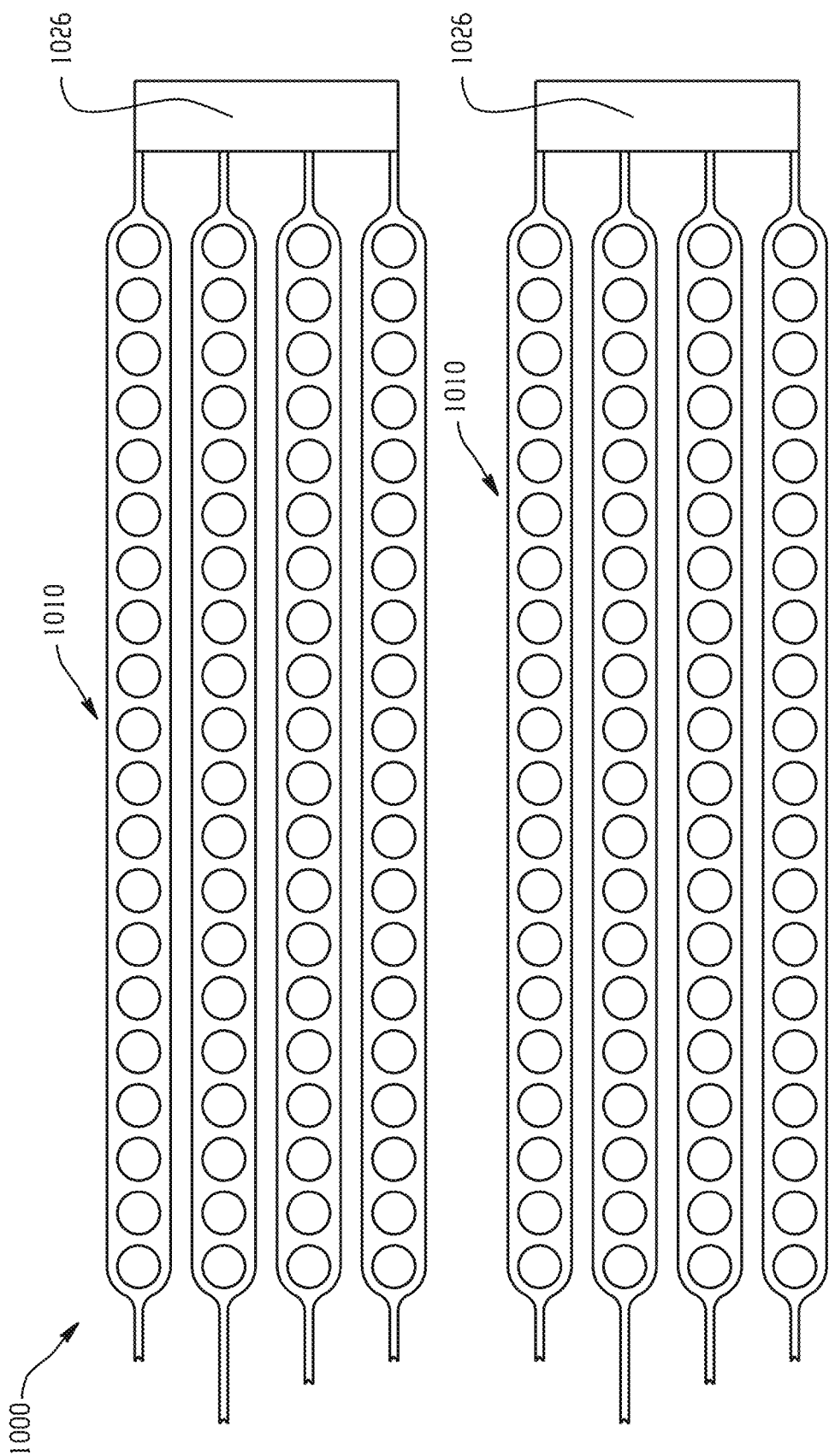
FIG. 15 is an exemplary photograph showing two neuromuscular cuff devices according to the embodiment of FIG. 14.

With reference to FIG. 15, two neuromuscular cuff devices 1010 according to the embodiment of FIG. 14 are shown. The cuff devices 1010 each include a fork 1026 for additional support when designing and/or placing the cuff devices 1010 over a damaged or degenerative neuromuscular region (not shown).

Figure 16:
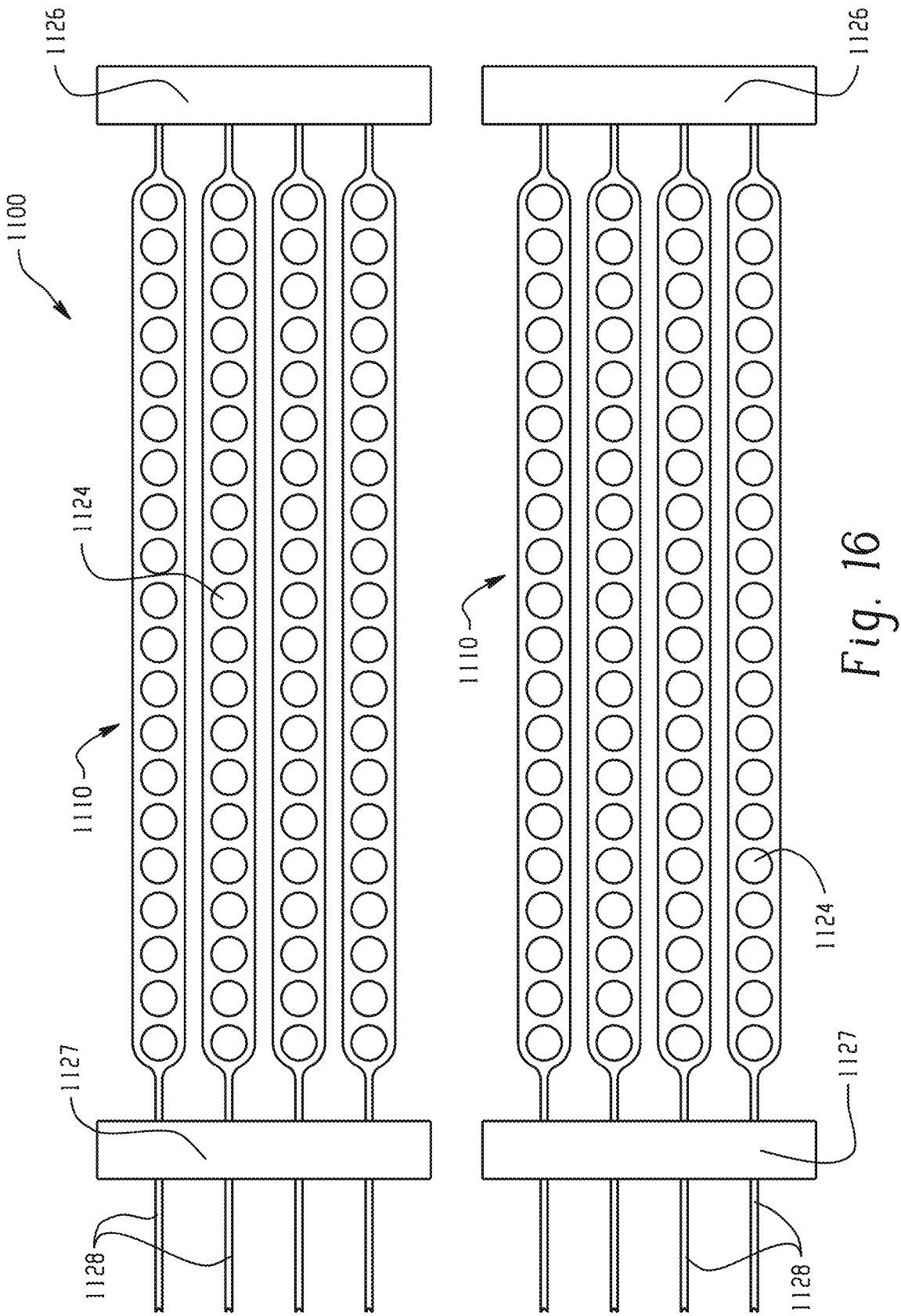
FIG. 16 is an exemplary photograph showing two neuromuscular cuff devices according to a different embodiment.

With reference to FIG. 16, two neuromuscular cuff devices 1100 according to a different embodiment are shown. A fork 1126 is provided at one end of each cuff for additional design and/or structural support, similar to the fork 626 in FIG. 6. Here, a second fork 1127 is also provided located along the headers 1128. Put another way, the fingers 1126 are bracketed by a fork on each end. The additional fork 1127 provides additional support in combination with fork 1126 for situations when the neuromuscular cuff 1110 must be stretched flat across a surface. Additional fork 1127 can also maintains fingers 1124 within the same damaged or degenerative neuromuscular region 1120 (not shown), which effectively concentrates stimulation and prevents flexibility.

Figure 17:
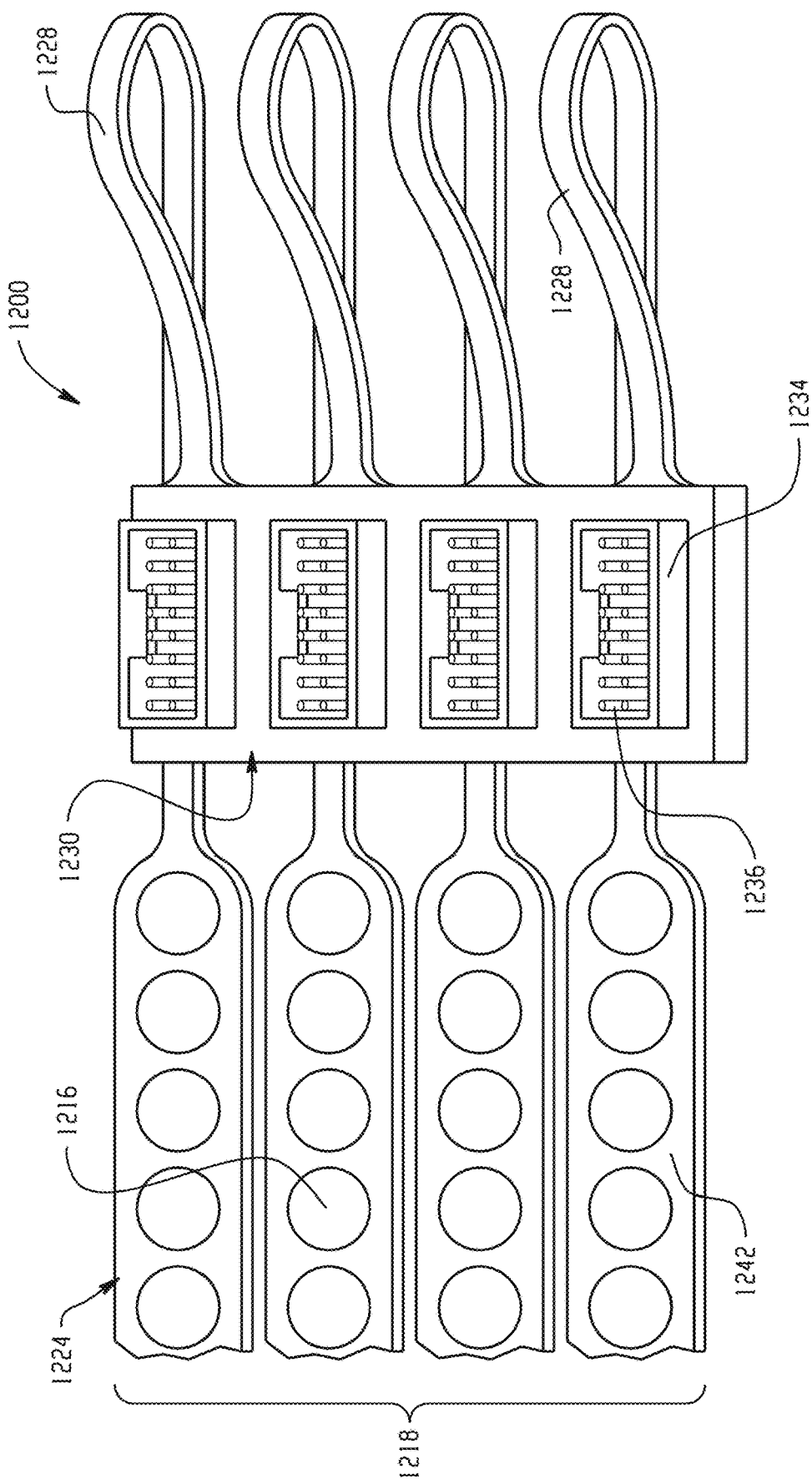
FIG. 17 is an exemplary photograph showing a rigidizer and the primary side of a neuromuscular cuff device according to yet another embodiment.

With reference to FIG. 17, the primary side of another embodiment of the neuromuscular cuff 1200 is shown. Hydrogel discs 1216 have been applied to electrodes 1214 (not shown, covered), forming an electrogel disc array 1218. Two of the four fingers 1224 still include the hydrogel tape before being separated from hydrogel discs 1216. Electrogel discs 1217 are not connected to each other within the array 1218 so that the electrogel discs 1217 may be independently stimulated.

While not exposed to the air, copper traces 1242 are viewable through the polyimide cover layer 700. A secondary side rigidizer 1230 is shown by folding the primary side over at the headers 1228. Connectors 1234 on the secondary side rigidizer 1230 allow for the neuromuscular stimulation cuff 1200 to be interfaced with the neural signal processor 104 (not shown). Each pin 1236 within connector 1234 is electrically connected with a single electrogel disc 1217.

Figure 18:
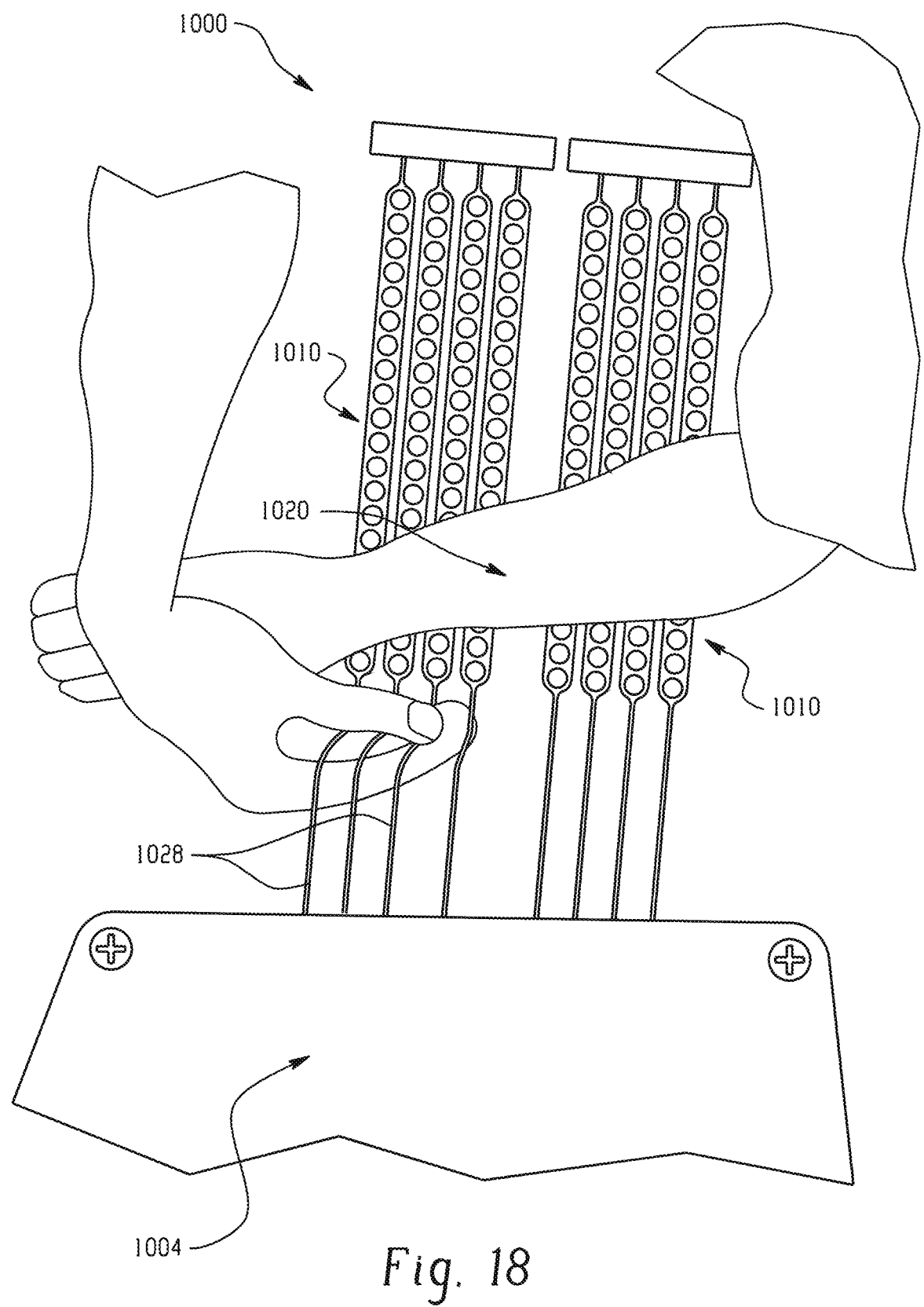
FIG. 18 is an exemplary photograph showing the positioning of a patient's arm region over two neuromuscular cuff devices according to the embodiment of FIG. 14.

With reference to FIG. 18, a patient's arm including damaged or degenerative neuromuscular region 1020 is placed over two neuromuscular cuff devices 1010 according to the embodiment of FIG. 14. Flexible headers 1028 may be used as support while positioning the device 1010 under an arm.

Figure 19:
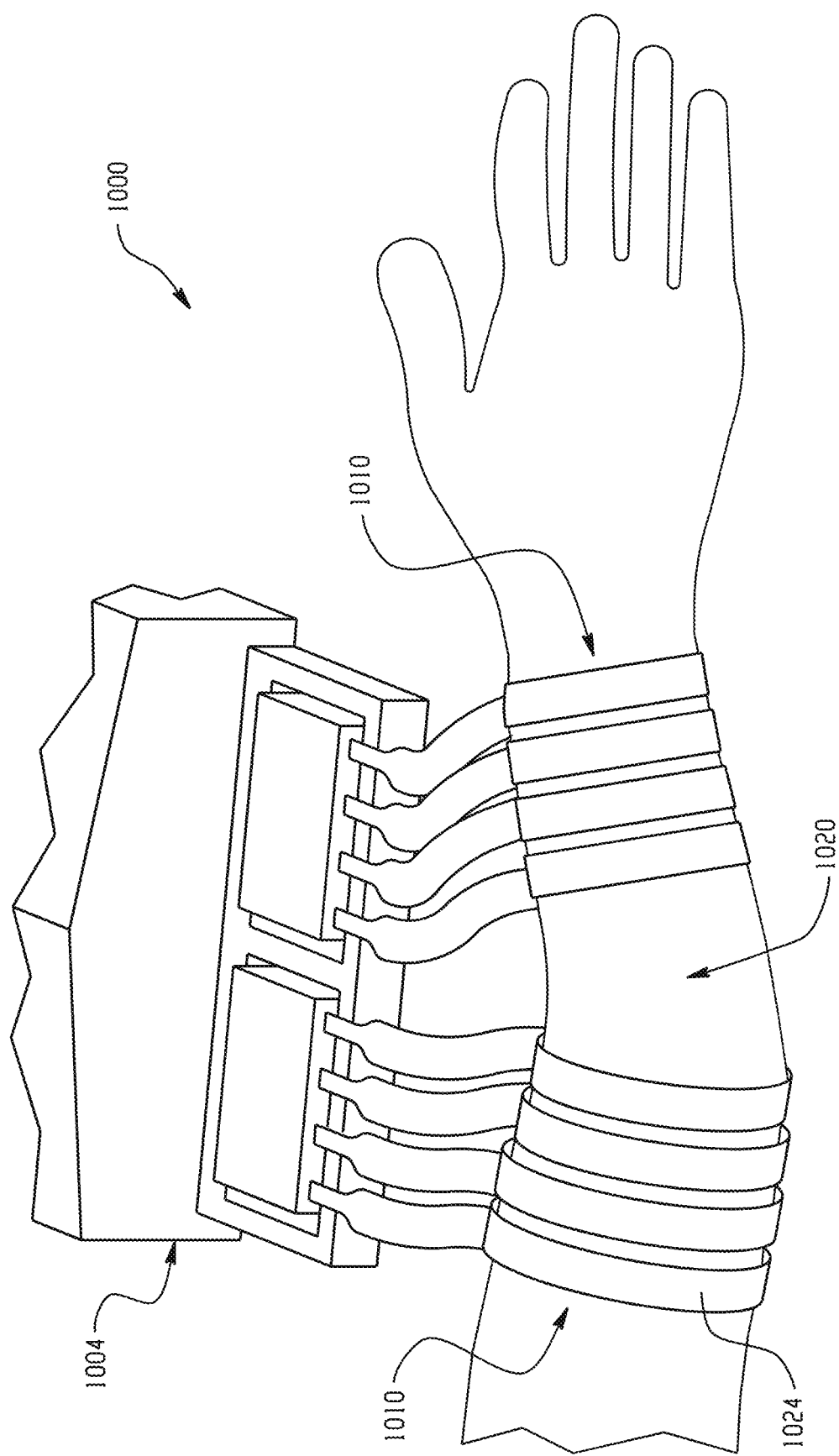
FIG. 19 is an exemplary photograph showing two neuromuscular cuff devices according to the embodiment of FIG. 14 which are wrapped around a patient's arm region in preparation for neuromuscular stimulation.

With reference to FIG. 19, two neuromuscular cuff devices 1010 in an exemplary embodiment are wrapped around a patient's arm region 1020 in preparation for neuromuscular stimulation. The two cuff devices 1010 together provide 160 separate electrodes for stimulating finger or wrist movements. Fingers 1024 the neuromuscular cuff to fit around the arm region 1020 at points of varying circumference. Hydrogel discs 1016 (not shown) keep both cuffs 1010 adhered to the arm.

Figure 20:
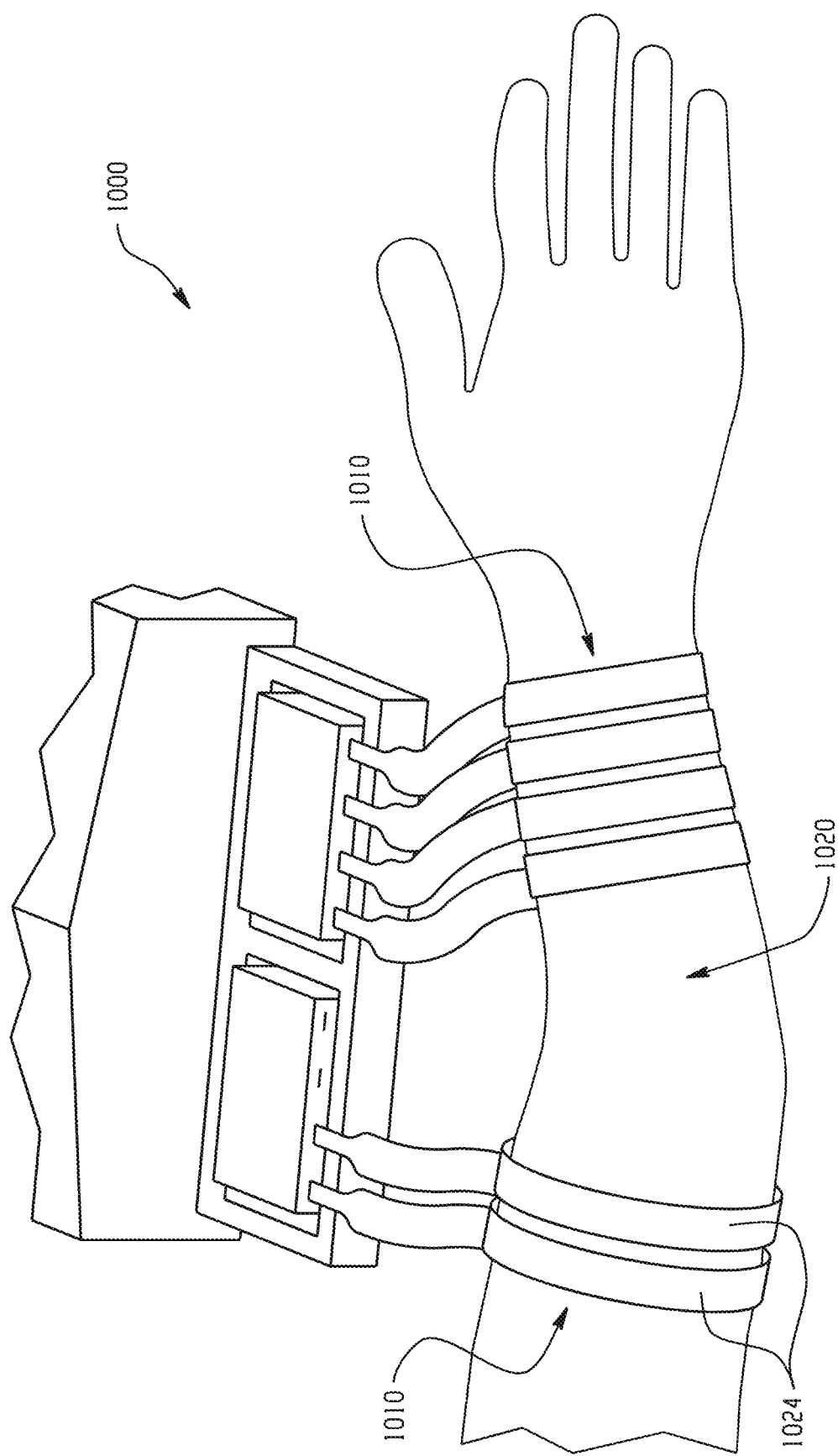
FIG. 20 is an exemplary photograph showing two neuromuscular cuff devices according to the embodiment of FIG. 14 which are alternatively wrapped around a patient's arm region in preparation for neuromuscular stimulation.

With reference to FIG. 20, two neuromuscular cuff devices 1010 according to the embodiment of FIG. 14 are alternatively wrapped around a patient's arm region in preparation for neuromuscular stimulation. Only two fingers 1024 of one of the neuromuscular cuff devices 1010 are being utilized in combination with all fingers 1024 on the other cuff device 1010. More or less electrodes can be used, as shown in FIG. 20, depending on the nature of the damage to a patent's neuromuscular region 1020 and the type of movement one wishes to reanimate through neuromuscular stimulation.

The present disclosure has been described with reference to exemplary embodiments. Obviously, modifications and alterations will occur to others upon reading and understanding the preceding detailed description. It is intended that the present disclosure be construed as including all such modifications and alterations insofar as they come within the scope of the appended claims or the equivalents thereof.

The invention claimed is:

1. A system for thought-controlled neuromuscular stimulation, comprising:
   a sensor for monitoring or recording neural signals;
   a neural signal processor for receiving neural signals and processing the neural signals into a re-encoded signal; and a neuromuscular stimulation cuff for delivering neuromuscular stimulation according to the re-encoded signal;

wherein the neuromuscular stimulation cuff comprises a plurality of flexible printed circuit boards arranged as a plurality of fingers, each finger having including:
a polyimide base layer; and
an etched conductive circuit layer fabricated onto the polyimide base layer, the etched conductive circuit layer including a plurality of electrodes disposed spaced along the finger.

2. The system of claim 1, wherein the neural signal processor decodes the neural signals according to a neural decoding algorithm.

3. The system of claim 1, wherein the neural signal processor re-encodes the neural signals according to a stimulation control algorithm.

4. The system of claim 1, wherein the stimulation control algorithm is altered by at least one of a training profile and position feedback data.

5. The system of claim 1, wherein the neural signals are transmitted wirelessly between the sensor and the neural signal processor.

6. The system of claim 1, wherein each finger further includes a coverlay layer disposed over the etched conductive circuit layer wherein the coverlay layer does not cover the central area of the electrodes.

7. The system of claim 6, wherein the coverlay layer comprises a polyimide layer that is thinner than the polyimide base layer.

8. The system of claim 1, further comprising a rigidizer comprising an inflexible circuit board that interfaces with the neural signal processor.

9. The system of claim 1, wherein on the neuromuscular stimulation cuff, a hydrogel disc covers each electrode.

10. The system of claim 1, wherein the etched conductive circuit layer is located adjacent to the surface of the polyimide base layer, and a coverlay layer is located adjacent to the etched conductive circuit layer.

11. The system of claim 10, wherein the etched conductive circuit layer further comprises a plurality of connective traces, and the coverlay layer covers the plurality of connective traces and a portion of each of the plurality of electrodes.

12. The system of claim 11, wherein the portion of each of the plurality of electrodes not covered by the coverlay layer is plated with a conductive metal.

13. The system of claim 1, wherein on the neuromuscular stimulation cuff, at least two adjacent fingers of the plurality of fingers are connected by a webbing.

14. The system of claim 1, wherein the neuromuscular stimulation cuff further includes a plurality of headers, each header connected to one of the fingers.

15. The system of claim 14, wherein each header is thinner than each finger.

16. The system of claim 1, wherein the flexible printed circuit of the neuromuscular stimulation cuff further comprises a silkscreen layer.

17. The system of claim 1 wherein the neuromuscular stimulation cuff further comprises:
a fork connecting the plurality of fingers; and
a rigidizer, the plurality of fingers extending between the fork and the rigidizer.

18. A method for thought-controlled neuromuscular stimulation, includes:
providing a neuromuscular stimulation cuff that comprises a plurality of flexible printed circuit boards arranged as a plurality of fingers, each finger including a polyimide base layer and an etched conductive circuit layer fabricated onto the polyimide base layer, wherein the etched conductive circuit layer includes a plurality of electrodes disposed spaced along the finger;
receiving neurological signals indicative of an intended action;
processing the neurological signals;
generating a re-encoded signal; and
delivering neuromuscular stimulation according to the re-encoded signal using the neuromuscular stimulation cuff to effectuate the intended action.

19. The method of claim 18, wherein the processing of the neurological signals includes decoding the neurological signals with at least one neural decoding algorithm.

20. The method of claim 18, wherein the processing of the neurological signals includes processing the neurological signals with at least one stimulation control algorithm.

21. The method of claim 18, wherein the delivering of the neuromuscular stimulation further includes altering the position of electrodes within the neuromuscular stimulation cuff to effectuate the intended action.

22. The method of claim 18, wherein the delivering of the neuromuscular stimulation further includes selectively delivering stimulation to at least one pair of electrodes within the neuromuscular stimulation cuff to effectuate the intended action.

23. The method of claim 18, further including recording EMG signals from a damaged neuromuscular region.

* * * * *